US011061043B2

United States Patent
Lai et al.

(10) Patent No.: US 11,061,043 B2
(45) Date of Patent: Jul. 13, 2021

(54) LOADING STATION

(71) Applicant: Cellular Research, Inc., Menlo Park, CA (US)

(72) Inventors: Janice H. Lai, Mountain View, CA (US); Philipp S. Spuhler, Redwood City, CA (US); Geoffrey R. Facer, Redwood City, CA (US); Sixing Li, Mountain View, CA (US); Christopher G. Cesar, Menlo Park, CA (US)

(73) Assignee: CELLULAR RESEARCH, INC., Menlo Park, CA (US)

( * ) Notice: Subject to any disclaimer, the term of this patent is extended or adjusted under 35 U.S.C. 154(b) by 0 days.

(21) Appl. No.: 16/824,318

(22) Filed: Mar. 19, 2020

(65) Prior Publication Data
US 2020/0217861 A1 Jul. 9, 2020

Related U.S. Application Data

(62) Division of application No. 15/677,827, filed on Aug. 15, 2017, now Pat. No. 10,634,691.

(51) Int. Cl.
*G01N 1/00* (2006.01)
*G01N 35/00* (2006.01)
*C12N 15/10* (2006.01)
*G01N 35/10* (2006.01)
*B01L 9/00* (2006.01)
*B01L 3/00* (2006.01)

(52) U.S. Cl.
CPC .... *G01N 35/0098* (2013.01); *B01L 3/502761* (2013.01); *B01L 9/527* (2013.01); *C12N 15/1013* (2013.01); *C12N 15/1065* (2013.01); *G01N 35/00029* (2013.01); *G01N 35/1095* (2013.01); *B01L 9/52* (2013.01); *B01L 2200/0668* (2013.01); *B01L 2300/0816* (2013.01); *B01L 2300/0819* (2013.01); *B01L 2300/0877* (2013.01); *B01L 2400/043* (2013.01); *G01N 2035/00158* (2013.01); *G01N 2035/00237* (2013.01); *G01N 2035/00306* (2013.01); *G01N 2035/1034* (2013.01)

(58) Field of Classification Search
CPC ..... G01N 2035/00574; G01N 35/0098; G01N 35/1011; G01N 33/54326
USPC ........................................ 436/174, 175, 176
See application file for complete search history.

(56) References Cited

U.S. PATENT DOCUMENTS

2006/0121612 A1* 6/2006 Tajima .................... A61P 35/00
   435/459
2011/0088491 A1 4/2011 Krueger

* cited by examiner

*Primary Examiner* — Natalia Levkovich
(74) *Attorney, Agent, or Firm* — Bret E. Field; Bozicevic, Field & Francis LLP

(57) ABSTRACT

Disclosed herein are methods, devices, and systems for loading and retrieval of particles. In some embodiments, a loading station comprise a tray configured to receive a microwell array, a first magnet, a second magnet, and an actuation mechanism configured to cause movement of at least one of the first magnet and the second magnet.

20 Claims, 14 Drawing Sheets

LOADING STATION

BACKGROUND

Field

The present disclosure relates generally to the field of sample loading, and more particularly, relates to systems, methods, and devices for loading and retrieval of particles.

Description of the Related Art

Methods and techniques such as stochastic barcoding are useful for single cell analysis, in particular deciphering gene expression profiles to determine the states of single cells using, for example, reverse transcription, polymerase chain reaction (PCR) amplification, and next generation sequencing (NGS). There is a need for methods and techniques for efficient loading of particles, such as barcode-bearing magnetic beads and cells onto a flowcell having one or more microwell arrays situated therein.

SUMMARY

In some embodiments, a loading station is disclosed. The loading station includes a tray configured to receive a microwell array. The loading station also includes a first magnet, the first magnet being movable between a first magnet active position in which the first magnet is positioned to exert a first magnetic force in a first direction on one or more magnetic particles positioned within the microwell array and a first magnet inactive position in which the first magnet is positioned to exert less magnetic force on the one or more magnetic particles positioned within the microwell array in comparison to the first magnet active position, wherein the first magnet is positioned inferior to the tray when the first magnet is in the first magnet active position. The loading station also includes a second magnet, the second magnet being movable between a second magnet active position in which the second magnet is positioned to exert a second magnetic force in a second direction on the one or more magnetic particles positioned within the microwell array and a second magnet inactive position in which the second magnet is positioned to exert less magnetic force on the one or more magnetic particles positioned within the microwell array in comparison to the second magnet active position, wherein the second direction of the second magnetic force is different than the first direction of the first magnetic force. The loading station also includes an actuation mechanism configured to cause movement of at least one of the first magnet and the second magnet.

In some embodiments, the actuation mechanism includes an actuator, the actuator being movable between a plurality of different positions, wherein at least some movements of the actuator cause movement of the first magnet between the first magnet active position and the first magnet inactive position, and wherein at least some movements of the actuator cause movement of the second magnet between the second magnet active position and the second magnet inactive position. In some embodiments, at least one of the first magnet and the second magnet are coupled to the actuation mechanism such that when the first magnet is in the first magnet active position, the second magnet is not in the second magnet active position and when the second magnet is in the second magnet active position, the first magnet is not in the first magnet active position. In some embodiments, each movement of the actuator is configured to cause the movement of no more than one of the first magnet and the second magnet. In some embodiments, the actuation mechanism includes one or more members coupled to the first magnet and one or more members coupled to the second magnet. In some embodiments, the actuator is configured to couple to the one or more members coupled to one of the first magnet or the second magnet in at least some of the plurality of different positions of the actuator, wherein the actuator is configured to decouple from the one or more members coupled to the one of the first magnet and the second magnet in at least some of the plurality of different positions. In some embodiments, the loading station includes a drawer configured to hold one or more tubes, the drawer being movable between a plurality of different positions. In some embodiments, the drawer is movable to at least one position in which at least one of the one or more tubes is positioned to align with an outlet of the microwell. In some embodiments, the loading station includes a drawer actuator, the drawer actuator being movable between a plurality of different positions, wherein at least some movements of the drawer actuator cause movement of the drawer. In some embodiments, the microwell array is housed within a cartridge and the tray is configured to receive the cartridge housing the microwell array.

In some embodiments a cartridge can be positioned within the tray of the loading station. In some embodiments, the cartridge includes a flowcell, wherein the flowcell includes the microwell array. In some embodiments, a superior surface of the first magnet is separated from an inferior surface of the flowcell by a distance of no more than 1.0 mm when the first magnet is positioned in the first magnet active position. In some embodiments, an inferior surface of the second magnet is separated from a superior surface of the flowcell by a distance of no more than 1.0 mm when the second magnet is positioned in the second magnet active position. In some embodiments, a superior surface of the first magnet is parallel to an inferior surface of the cartridge when the first magnet is in the first magnet active position. In some embodiments, an inferior surface of the second magnet is parallel to a superior surface of the cartridge when the second magnet is in the second magnet active position. In some embodiments, the loading station includes a locking mechanism configured to releasably secure the cartridge within the tray.

In some embodiments, a method for collecting a plurality of barcode-bearing beads is disclosed. The method includes introducing a plurality of cells into a flowcell of a cartridge positioned within a loading station, introducing a plurality of magnetic barcode-bearing beads into the flowcell, wherein the flowcell includes a plurality of microwells, wherein each microwell is dimensioned to receive at least one cell of the plurality of cells and at least one magnetic barcode-bearing bead of the plurality of magnetic barcode-bearing beads, moving a first magnet of the loading station to a position sufficient to exert a first magnetic force on at least some of the magnetic barcode-bearing beads positioned within the plurality of microwells in a first direction, moving a second magnet of the loading station to a position sufficient to exert a second magnetic force on at least some of the magnetic barcode-bearing beads positioned within the plurality of microwells in a second direction different than the first direction, and introducing a fluid into the flowcell to cause at least some of the barcode-bearing beads to flow through the flowcell.

In some embodiments, at least one of the first magnetic force and the second magnetic force are of a magnitude sufficient to prevent magnetic barcode-bearing beads on which the at least one of the first magnetic force and second magnetic force are exerted from flowing through the flowcell when the fluid is introduced into the flowcell. In some embodiments, each of the first magnet and the second magnet are coupled to an actuation mechanism includes an actuator. In some embodiments, moving the first magnet of the loading station to exert a first magnetic force on at least some of the magnetic barcode-bearing beads positioned within the plurality of microwells in a first direction includes moving the actuator to a first actuator position. In some embodiments, moving the second magnet of the loading station to exert a second magnetic force on at least some of the magnetic barcode-bearing beads positioned within the plurality of microwells in a second direction different than the first direction includes moving the actuator to a second actuator position from the first actuator position. In some embodiments, moving the actuator from the first actuator position to the second actuator position causes the first magnet to move to a position in which less magnetic force is exerted on the at least some of the magnetic barcode-bearing beads positioned within the plurality of microwells by the first magnet than when the actuator is positioned within the first position.

BRIEF DESCRIPTION OF THE DRAWINGS

The features of the present disclosure will become more fully apparent from the following description and appended claims, taken in conjunction with the accompanying drawings. Understanding that these drawings depict only several embodiments in accordance with the disclosure and are not to be considered limiting of its scope, the disclosure will now be described with additional specificity and detail through use of the accompanying drawings.

DETAILED DESCRIPTION

Figure 1:
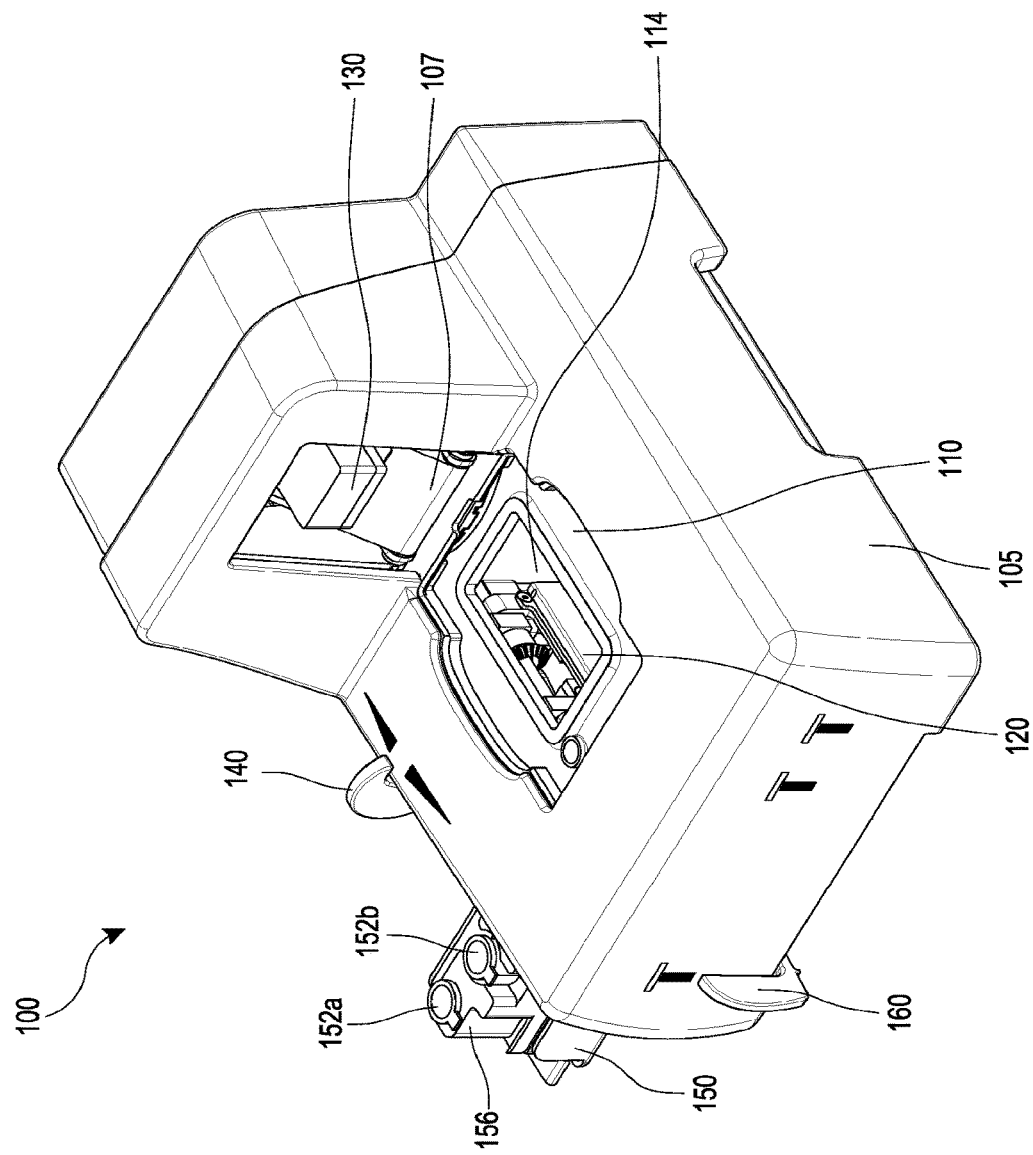
FIG. 1 is a perspective view of a loading station according to an exemplary preferred embodiment.

The following detailed description is directed to certain specific embodiments. The invention(s) disclosed herein, however, can be embodied in a multitude of different ways as defined and covered by the claims. In this description, reference is made to the drawings, wherein like parts are designated with like numerals throughout. The features, aspects and advantages of the present invention will now be described with reference to the drawings of several embodiments that are intended to be within the scope of the development herein disclosed. These and other embodiments will become readily apparent to those skilled in the art from the following detailed description of the embodiments having reference to the attached figures, the invention not being limited to any particular embodiment(s) herein disclosed.

All patents, published patent applications, and other publications referred to herein are incorporated by reference in their entirety with respect to the related technology.

Methods and systems for stochastic barcoding are disclosed. In some embodiments, a device comprises: a flowcell comprising a fluidic channel, an inlet port, and an outlet port, wherein the fluidic channel comprises a ceiling, a first sidewall, and a bottom, wherein the contact angle of the ceiling is at least 10 degrees smaller than the contact angle of the first sidewall, wherein the bottom of the fluidic channel comprises a substrate which comprises a plurality of microwells, and wherein the inlet port and the outlet port are in fluid communication with the flowcell via the fluidic channel. The fluidic channel can comprise a second sidewall. In some embodiments, the hydrophilic coating is offset from the edge formed by the ceiling and first sidewall by, for example, 100-1000 micrometers or 1%-25% of the width of the ceiling. Such a device can be used to create plug flow across the width of the flowcell chamber. Plug flow can enable efficient loading and retrieval of particles such as beads and cells into and from microwells of a microwell array at the bottom of the flowcell chamber.

A superhydrophilic coating or treatment of the top wall (also referred to as ceiling, flowcell ceiling, or fluidic channel ceiling) within the fluidic channel of a flowcell can be used to introduce gas plugs and buffer plugs to a flowcell with horizontal non-tilting workflow (i.e., without tilting the flowcell). The superhydrophilic coating provides capillary aided flow for a uniform fluid front of the gas and buffer plug without the use of buoyancy to achieve gas displacement by buffer or to achieve buffer displacement by the gas. Thus, the requirement to utilize buoyancy to displace the gas with buffer or to displace buffer with the gas, may be eliminated. In turn, the requirement of non-horizontal tilting workflow of the flow-cell may be eliminated. In some embodiments, structured hydrophilic and hydrophobic coatings can be used on a flowcell ceiling or a fluidic channel ceiling to tailor the profile of a gas-buffer fluid front in a flowcell. The selective coating (also referred to as functionalization) of the fluidic channel boundary (also referred to as the flowcell boundary) influences the direction of capillary flow within specific portions of the flowcell to control the profile of the gas-buffer fluid front profile. Capillary aided flow can be utilized for horizontal operation of a flowcell with gas-buffer plug flow in order to avoid breakdown of the buffer and gas plugs. Additionally, plug flow can be utilized to achieve high flow velocities at the flowcell boundaries. One purpose for this may be to flush away excess beads on the surface of a microwell array within the flowcell.

Also disclosed herein are methods, systems, and devices for sample loading. In some embodiments, a method comprises: (a) providing a device that comprises: a flowcell comprising a fluidic channel, an inlet port, and an outlet port, wherein the fluidic channel comprises a fluidic channel ceiling, a first sidewall, and a bottom wherein the contact angle of the fluidic channel ceiling is at least 10 degrees smaller than the contact angle of the first sidewall, wherein the bottom comprises a substrate which comprises a plurality of microwells, wherein the plurality of microwells comprises at least 100 microwells, and wherein the inlet port and the outlet port are in fluid communication with the flowcell via the fluidic channel; (b) introducing a gas into the fluidic channel via the inlet port; and (c) introducing a first sample into the fluidic channel via the inlet port, wherein the first sample comprises a first plurality of particles, and wherein, after introducing the sample into the fluidic channel via the inlet port, at least 25% of the plurality of microwells each contains a single particle of the first plurality of particles. In some embodiments, at least 50% or 75% of the plurality of microwells each contains a single particle of the first plurality of particles. The fluidic channel can comprise a second sidewall.

Definitions

Unless defined otherwise, technical and scientific terms used herein have the same meaning as commonly understood by one of ordinary skill in the art to which the present disclosure belongs. See, e.g. Singleton et al., Dictionary of Microbiology and Molecular Biology 2nd ed., J. Wiley & Sons (New York, N.Y. 1994); Sambrook et al., Molecular Cloning, A Laboratory Manual, Cold Springs Harbor Press (Cold Springs Harbor, N Y 1989). For purposes of the present disclosure, the following terms are defined below.

As used herein, the term "adaptor" can mean a sequence to facilitate amplification or sequencing of associated nucleic acids. The associated nucleic acids can comprise target nucleic acids. The associated nucleic acids can comprise one or more of spatial labels, target labels, sample labels, indexing label, barcodes, stochastic barcodes, or molecular labels. The adaptors can be linear. The adaptors can be pre-adenylated adapters. The adaptors can be double- or single-stranded. One or more adaptor can be located on the 5' or 3' end of a nucleic acid. When the adaptors comprise known sequences on the 5' and 3' ends, the known sequences can be the same or different sequences. An adaptor located on the 5' and/or 3' ends of a polynucleotide can be capable of hybridizing to one or more oligonucleotides immobilized on a surface. An adapter can, in some embodiments, comprise a universal sequence. A universal sequence can be a region of nucleotide sequence that is common to two or more nucleic acid molecules. The two or more nucleic acid molecules can have regions of different sequence. Thus, for example, the 5' adapters can comprise identical and/or universal nucleic acid sequences and the 3' adapters can comprise identical and/or universal sequences.

As used herein the term "associated" or "associated with" can mean that two or more species are identifiable as being co-located at a point in time. An association can mean that two or more species are or were within a similar container. An association can be an informatics association, where for example digital information regarding two or more species is stored and can be used to determine that one or more of the species were co-located at a point in time. An association can be a physical association. In some embodiments, two or more associated species are "tethered", "attached", or "immobilized" to one another or to a common solid or semisolid surface. An association may refer to covalent or non-covalent means for attaching labels to solid or semi-solid supports such as beads. An association may be a covalent bond between a target and a label.

As used herein, the term "digital counting" can refer to a method for estimating a number of target molecules in a sample. Digital counting can include the step of determining a number of unique labels that have been associated with targets in a sample. This stochastic methodology transforms the problem of counting molecules from one of locating and identifying identical molecules to a series of yes/no digital questions regarding detection of a set of predefined labels.

As used herein, the term "label" or "labels" can refer to nucleic acid codes associated with a target within a sample. A label can be, for example, a nucleic acid label. A label can be an entirely or partially amplifiable label. A label can be entirely or partially sequencable label. A label can be a portion of a native nucleic acid that is identifiable as distinct. A label can be a known sequence. A label can comprise a junction of nucleic acid sequences, for example a junction of a native and non-native sequence. As used herein, the term "label" can be used interchangeably with the terms, "index", "tag," or "label-tag." Labels can convey information. For example, in various embodiments, labels can be used to determine an identity of a sample, a source of a sample, an identity of a cell, and/or a target.

As used herein, the term "nucleic acid" refers to a polynucleotide sequence, or fragment thereof. A nucleic acid can comprise nucleotides. A nucleic acid can be exogenous or endogenous to a cell. A nucleic acid can exist in a cell-free environment. A nucleic acid can be a gene or fragment thereof. A nucleic acid can be DNA. A nucleic acid can be RNA. A nucleic acid can comprise one or more analogs (e.g. altered backbone, sugar, or nucleobase). Some non-limiting examples of analogs include: 5-bromouracil, peptide nucleic acid, xeno nucleic acid, morpholinos, locked nucleic acids, glycol nucleic acids, threose nucleic acids, dideoxynucleotides, cordycepin, 7-deaza-GTP, fluorophores (e.g. rhodamine or fluorescein linked to the sugar), thiol containing nucleotides, biotin linked nucleotides, fluorescent base analogs, CpG islands, methyl-7-guanosine, methylated nucleotides, inosine, thiouridine, pseudouridine, dihydrouridine, queuosine, and wyosine. "Nucleic acid", "polynucleotide, "target polynucleotide", and "target nucleic acid" can be used interchangeably.

As used herein, the term "sample" can refer to a composition comprising targets. Suitable samples for analysis by the disclosed methods, devices, and systems include cells, tissues, organs, or organisms.

As used herein, the term "sampling device" or "device" can refer to a device which may take a section of a sample and/or place the section on a substrate. A sample device can refer to, for example, a fluorescence activated cell sorting (FACS) machine, a cell sorter machine, a biopsy needle, a biopsy device, a tissue sectioning device, a microfluidic device, a blade grid, and/or a microtome.

As used herein, the term "solid support" can refer to discrete solid or semi-solid surfaces to which a plurality of stochastic barcodes may be attached. A solid support may encompass any type of solid, porous, or hollow sphere, ball, bearing, cylinder, or other similar configuration composed of plastic, ceramic, metal, or polymeric material (e.g., hydrogel) onto which a nucleic acid may be immobilized (e.g., covalently or non-covalently). A solid support may comprise a discrete particle that may be spherical (e.g., microspheres) or have a non-spherical or irregular shape, such as cubic, cuboid, pyramidal, cylindrical, conical, oblong, or disc-shaped, and the like. A plurality of solid supports spaced in an array may not comprise a substrate. A solid support may be used interchangeably with the term "bead."

A solid support can refer to a "substrate." A substrate can be a type of solid support. A substrate can refer to a continuous solid or semi-solid surface on which the methods of the disclosure may be performed. A substrate can refer to an array, a cartridge, a chip, a device, and a slide, for example.

As used herein, the term "stochastic barcode" can refer to a polynucleotide sequence comprising labels. A stochastic barcode can be a polynucleotide sequence that can be used for stochastic barcoding. Stochastic barcodes can be used to quantify targets within a sample. Stochastic barcodes can be used to control for errors which may occur after a label is associated with a target. For example, a stochastic barcode can be used to assess amplification or sequencing errors. A stochastic barcode associated with a target can be called a stochastic barcode-target or stochastic barcode-tag-target.

As used herein, the term "gene-specific stochastic barcode" can refer to a polynucleotide sequence comprising labels and a target-binding region that is gene-specific. A stochastic barcode can be a polynucleotide sequence that can be used for stochastic barcoding. Stochastic barcodes can be used to quantify targets within a sample. Stochastic barcodes can be used to control for errors which may occur after a label is associated with a target. For example, a stochastic barcode can be used to assess amplification or sequencing errors. A stochastic barcode associated with a target can be called a stochastic barcode-target or stochastic barcode-tag-target.

As used herein, the term "stochastic barcoding" can refer to the random labeling (e.g., barcoding) of nucleic acids. Stochastic barcoding can utilize a recursive Poisson strategy to associate and quantify labels associated with targets. As used herein, the term "stochastic barcoding" can be used interchangeably with "gene-specific stochastic barcoding."

As used here, the term "target" can refer to a composition which can be associated with a stochastic barcode. Exemplary suitable targets for analysis by the disclosed methods, devices, and systems include oligonucleotides, DNA, RNA, mRNA, microRNA, tRNA, and the like. Targets can be single or double stranded. In some embodiments targets can be proteins. In some embodiments targets are lipids.

Stochastic Barcodes

Stochastic barcoding has been described in, for example, US20150299784, WO2015031691, and Fu et al, Proc Natl Acad Sci U.S.A. 2011 May 31; 108(22):9026-31, the content of these publications is incorporated hereby in its entirety. Briefly, a stochastic barcode can be a polynucleotide sequence that may be used to stochastically label (e.g., barcode, tag) a target. A stochastic barcode can comprise one or more labels. Exemplary labels can include a universal label, a cellular label, a molecular label, a sample label, a plate label, a spatial label, and/or a pre-spatial label. The stochastic barcode can comprise a 5' amine that may link the stochastic barcode to a solid support. The stochastic barcode can comprise a universal label, a dimension label, a spatial label, a cellular label, and/or a molecular label. The order of different labels (including but not limited to the universal label, the dimension label, the spatial label, the cellular label, and the molecule label) in the stochastic barcode can vary. For example, the universal label may be the 5'-most label, and the molecular label may be the 3'-most label. The spatial label, dimension label, and the cellular label may be in any order. In some embodiments, the universal label, the spatial label, the dimension label, the cellular label, and the molecular label are in any order.

The stochastic barcodes can be from a "non-depleting reservoirs," a pool of stochastic barcodes made up of many different labels. A non-depleting reservoir can comprise large numbers of different stochastic barcodes such that when the non-depleting reservoir is associated with a pool of targets each target is likely to be associated with a unique stochastic barcode. The uniqueness of each labeled target molecule can be determined by the statistics of random choice, and depends on the number of copies of identical target molecules in the collection compared to the diversity of labels. The size of the resulting set of labeled target molecules can be determined by the stochastic nature of the barcoding process, and analysis of the number of stochastic barcodes detected then allows calculation of the number of target molecules present in the original collection or sample. When the ratio of the number of copies of a target molecule present to the number of unique stochastic barcodes is low, the labeled target molecules are highly unique (i.e. there is a very low probability that more than one target molecule will have been labeled with a given label).

A label, for example the cellular label, can comprise a unique set of nucleic acid sub-sequences of defined length, e.g. seven nucleotides each (equivalent to the number of bits used in some Hamming error correction codes), which can be designed to provide error correction capability. The set of error correction sub-sequences comprise seven nucleotide sequences can be designed such that any pairwise combination of sequences in the set exhibits a defined "genetic distance" (or number of mismatched bases), for example, a set of error correction sub-sequences can be designed to exhibit a genetic distance of three nucleotides. In this case, review of the error correction sequences in the set of sequence data for labeled target nucleic acid molecules (described more fully below) can allow one to detect or correct amplification or sequencing errors. In some embodiments, the length of the nucleic acid sub-sequences used for creating error correction codes can vary, for example, they can be, or be about 1, 2, 3, 4, 5, 6, 7, 8, 9, 10, 15, 20, 30, 31, 40, 50, or a number or a range between any two of these values, nucleotides in length. In some embodiments, nucleic acid sub-sequences of other lengths can be used for creating error correction codes.

The stochastic barcode can comprise a target-binding region. The target-binding region can interact with a target in a sample. The target can be, or comprise, ribonucleic acids (RNAs), messenger RNAs (mRNAs), microRNAs, small interfering RNAs (siRNAs), RNA degradation products, RNAs each comprising a poly(A) tail, and any combination thereof. In some embodiments, the plurality of targets can include deoxyribonucleic acids (DNAs).

In some embodiments, a target-binding region can comprise an oligo(dT) sequence which can interact with poly(A) tails of mRNAs. One or more of the labels of the stochastic barcode (e.g., the universal label, the dimension label, the spatial label, the cellular label, and the molecular label) can be separated by a spacer from another one or two of the remaining labels of the stochastic barcode. The spacer can be, for example, 1, 2, 3, 4, 5, 6, 7, 8, 9, 10, 11, 12, 13, 14, 15, 16, 17, 18, 19, or 20 or more nucleotides. In some embodiments, none of the labels of the stochastic barcode is separated by spacer.

A stochastic barcode can comprise one or more universal labels, one or more dimension labels, one or more spatial labels, one or more cellular labels, one or more molecular labels, one or more target binding regions, or any combination thereof.

The one or more universal labels can be the same for all stochastic barcodes in the set of stochastic barcodes attached to a given solid support (e.g., beads), or the same for all stochastic barcodes attached to a plurality of beads. A universal label can comprise a nucleic acid sequence that is capable of hybridizing to a sequencing primer. A universal label can comprise a nucleic acid sequence that is capable of hybridizing to a PCR primer, or comprise a nucleic acid sequence that is capable of hybridizing to a sequencing primer and a PCR primer. The nucleic acid sequence of the universal label that is capable of hybridizing to a sequencing or PCR primer can be referred to as a primer binding site. A universal label can comprise a sequence that can be used to initiate transcription of the stochastic barcode. A universal label can comprise a sequence that can be used for extension of the stochastic barcode or a region within the stochastic barcode.

A dimension label can comprise a nucleic acid sequence that provides information about a dimension in which the stochastic labeling occurred. For example, a dimension label can provide information about the time at which a target was stochastically barcoded. A dimension label can be associated with a time of stochastic barcoding in a sample. A dimension label can be activated at the time of stochastic labeling. Different dimension labels can be activated at different times. The dimension label provides information about the order in which targets, groups of targets, and/or samples were stochastically barcoded. For example, a population of cells can be stochastically barcoded at the G0 phase of the cell cycle. The cells can be pulsed again with stochastic barcodes at the G1 phase of the cell cycle. The cells can be pulsed again with stochastic barcodes at the S phase of the cell cycle, and so on. Stochastic barcodes at each pulse (e.g., each phase of the cell cycle), can comprise different dimension labels. In this way, the dimension label provides information about which targets were labeled at which phase of the cell cycle. Dimension labels can interrogate many different biological times. Exemplary biological times can include, but are not limited to, the cell cycle, transcription (e.g., transcription initiation), and transcript degradation. In another example, a sample (e.g., a cell, a population of cells) can be stochastically labeled before and/or after treatment with a drug and/or therapy. The changes in the number of copies of distinct targets can be indicative of the sample's response to the drug and/or therapy.

A dimension label can be activatable. An activatable dimension label can be activated at a specific time point. The activatable label can be, for example, constitutively activated (e.g., not turned off). The activatable dimension label can be, for example, reversibly activated (e.g., the activatable dimension label can be turned on and turned off).

A spatial label can comprise a nucleic acid sequence that provides information about the spatial orientation of a target molecule which is associated with the stochastic barcode. A spatial label can be associated with a coordinate in a sample. The coordinate can be a fixed coordinate. For example a coordinate can be fixed in reference to a substrate. A spatial label can be in reference to a two or three-dimensional grid. A coordinate can be fixed in reference to a landmark. The landmark can be identifiable in space. A landmark can be a structure which can be imaged. A landmark can be a biological structure, for example an anatomical landmark; or a cellular landmark, for instance an organelle. A landmark can be a non-natural landmark such as a structure with an identifiable identifier such as a color code, bar code, magnetic property, fluorescents, radioactivity, or a unique size or shape. A spatial label can be associated with a physical partition (e.g. a well, a container, or a droplet). In some embodiments, multiple spatial labels are used together to encode one or more positions in space. The spatial label can be identical for all stochastic barcodes attached to a given solid support (e.g., bead), but different for different solid supports (e.g., beads). A cellular label can comprise a nucleic acid sequence that provides information for determining which target nucleic acid originated from which cell. In some embodiments, the cellular label is identical for all stochastic barcodes attached to a given solid support (e.g., bead), but different for different solid supports (e.g., beads). In some embodiments, the percentage of stochastic barcodes on the same solid support comprising the same cellular label can be, or be about 60%, 70%, 80%, 85%, 90%, 95%, 97%, 99%, 100%, or a number or a range between any two of these values. For example, at least 95% of stochastic barcodes on the same solid support can comprise the same cellular label.

A molecular label can comprise a nucleic acid sequence that provides identifying information for the specific type of target nucleic acid species hybridized to the stochastic barcode. A molecular label can comprise a nucleic acid sequence that provides a counter for the specific occurrence of the target nucleic acid species hybridized to the stochastic barcode (e.g., target-binding region). In some embodiments, a diverse set of molecular labels are attached to a given solid support (e.g., bead). In some embodiments, there can be, or be about, $10^2$, $10^3$, $10^4$, $10^5$, $10^6$, $10^7$, $10^8$, $10^9$, or a number or a range of unique molecular label sequences. For example, a plurality of stochastic barcodes can comprise about 6561 molecular labels with distinct sequences. As another example, a plurality of stochastic barcodes can comprise about 65536 molecular labels with distinct sequences. In some embodiments, there can be at least, or at most, $10^2$, $10^3$, $10^4$, $10^5$, $10^6$, $10^7$, $10^8$, or $10^9$, unique molecular label sequences. The unique molecular label sequences attached to a given solid support (e.g., bead).

A target-binding region can hybridize with a target of interest. In some embodiments, the target binding regions can comprise a nucleic acid sequence that hybridizes specifically to a target (e.g. target nucleic acid, target molecule, e.g., a cellular nucleic acid to be analyzed), for example to a specific gene sequence. In some embodiments, a target binding region can comprise a nucleic acid sequence that can attach (e.g., hybridize) to a specific location of a specific target nucleic acid. In some embodiments, the target binding region can comprise a nucleic acid sequence that is capable of specific hybridization to a restriction enzyme site overhang (e.g. an EcoRI sticky-end overhang). The stochastic barcode can then ligate to any nucleic acid molecule comprising a sequence complementary to the restriction site overhang.

In some embodiments, a target binding region can comprise a non-specific target nucleic acid sequence. A non-specific target nucleic acid sequence can refer to a sequence that can bind to multiple target nucleic acids, independent of the specific sequence of the target nucleic acid. For example, target binding region can comprise a random multimer sequence, or an oligo(dT) sequence that hybridizes to the poly(A) tail on mRNA molecules. A random multimer sequence can be, for example, a random dimer, trimer, quatramer, pentamer, hexamer, septamer, octamer, nonamer, decamer, or higher multimer sequence of any length. In some embodiments, the target binding region is the same for all stochastic barcodes attached to a given bead. In some embodiments, the target binding regions for the plurality of stochastic barcodes attached to a given bead can comprise two or more different target binding sequences. A target binding region can be, or be about, 5, 10, 15, 20, 25, 30, 35, 40, 45, 50, or a number or a range between any two of these values, nucleotides in length. A target binding region can be at most about 5, 10, 15, 20, 25, 30, 35, 40, 45, 50 or more nucleotides in length.

In some embodiments, a target-binding region can comprise an oligo(dT) which can hybridize with mRNAs comprising poly-adenylated ends. A target-binding region can be gene-specific. For example, a target-binding region can be configured to hybridize to a specific region of a target. A target-binding region can be, or be about, 1, 2, 3, 4, 5, 6, 7, 8, 9, 10, 11, 12, 13, 14, 15, 16, 17, 18, 19, 20, 21, 22, 23, 24, 25, 26 27, 28, 29, 30, or a number or a range between any two of these values, nucleotides in length. A target-binding region can be at least, or at most, 1, 2, 3, 4, 5, 6, 7, 8, 9, 10, 11, 12, 13, 14, 15, 16, 17, 18, 19, 20, 21, 22, 23, 24, 25, 26 27, 28, 29, or 30, nucleotides in length. A target-binding region can be about 5-30 nucleotides in length. When a stochastic barcode comprises a gene-specific target-binding region, the stochastic barcode can be referred to as a gene-specific stochastic barcode.

Solid Supports

Stochastic barcodes disclosed herein can, in some embodiments, be associated with a solid support. The solid support can be, for example, a synthetic particle. In some embodiments, some or all of the molecular labels (e.g., the first molecular labels) of a plurality of stochastic barcodes (e.g., the first plurality of stochastic barcodes) on a solid support differ by at least one nucleotide. The cellular labels of the stochastic barcodes on the same solid support can be the same. The cellular labels of the stochastic barcodes on different solid supports can differ by at least one nucleotide. For example, first cellular labels of a first plurality of stochastic barcodes on a first solid support can have the same sequence, and second cellular labels of a second plurality of stochastic barcodes on a second solid support can have the same sequence. The first cellular labels of the first plurality of stochastic barcodes on the first solid support and the second cellular labels of the second plurality of stochastic barcodes on the second solid support can differ by at least one nucleotide. A cellular label can be, for example, about 5-20 nucleotides long. A molecular label can be, for example, about 5-20 nucleotides long.

The synthetic particle can be, for example, a bead. The bead can be, for example, a silica gel bead, a controlled pore glass bead, a magnetic bead, a Dynabead, a Sephadex/Sepharose bead, a cellulose bead, a polystyrene bead, or any combination thereof. The bead can comprise a material such as polydimethylsiloxane (PDMS), polystyrene, glass, polypropylene, agarose, gelatin, hydrogel, paramagnetic, ceramic, plastic, glass, methylstyrene, acrylic polymer, titanium, latex, sepharose, cellulose, nylon, silicone, or any combination thereof.

For example, after introducing cells such as single cells onto a plurality of microwells of a microwell array, beads can be introduced onto the plurality of microwells of the microwell array. Each microwell can comprise one bead. The beads can comprise a plurality of stochastic barcodes. A stochastic barcode can comprise a 5' amine region attached to a bead. The stochastic barcode can comprise a universal label, a molecular label, a target-binding region, or any combination thereof.

The stochastic barcodes disclosed herein can be associated to (e.g., attached to) a solid support (e.g., a bead). The stochastic barcodes associated with a solid support can each comprise a molecular label selected from a group comprising at least 100 or 1000 molecular labels with unique sequences. In some embodiments, different stochastic barcodes associated with a solid support can comprise molecular labels of different sequences. In some embodiments, a percentage of stochastic barcodes associated with a solid support comprises the same cell label. For example, the percentage can be, or be about 60%, 70%, 80%, 85%, 90%, 95%, 97%, 99%, 100%, or a number or a range between any two of these values. As another example, the percentage can be at least, or at most 60%, 70%, 80%, 85%, 90%, 95%, 97%, 99%, or 100%. In some embodiments, stochastic barcodes associated with a solid support can have the same cell label. The stochastic barcodes associated with different solid supports can have different cell labels selected from a group comprising at least 100 or 1000 cell labels with unique sequences.

In some embodiments, stochastically barcoding the plurality of targets in the sample can be performed with a solid support including a plurality of synthetic particles associated with the plurality of stochastic barcodes. In some embodiments, the solid support can include a plurality of synthetic particles associated with the plurality of stochastic barcodes. The spatial labels of the plurality of stochastic barcodes on different solid supports can differ by at least one nucleotide. The solid support can, for example, include the plurality of stochastic barcodes in two dimensions or three dimensions. The synthetic particles can be beads. The beads can be silica gel beads, controlled pore glass beads, magnetic beads, Dynabeads, Sephadex/Sepharose beads, cellulose beads, polystyrene beads, or any combination thereof. The solid support can include a polymer, a matrix, a hydrogel, a needle array device, an antibody, or any combination thereof. In some embodiments, the solid supports can be free floating. In some embodiments, the solid supports can be embedded in a semi-solid or solid array. The stochastic barcodes may not be associated with solid supports. The stochastic barcodes can be individual nucleotides. The stochastic barcodes can be associated with a substrate.

As used herein, the terms "tethered", "attached", and "immobilized" are used interchangeably, and can refer to covalent or non-covalent means for attaching stochastic barcodes to a solid support. Any of a variety of different solid supports can be used as solid supports for attaching pre-synthesized stochastic barcodes or for in situ solid-phase synthesis of stochastic barcode.

In some embodiments, the solid support is a bead. The bead can comprise one or more types of solid, porous, or hollow sphere, ball, bearing, cylinder, or other similar configuration which a nucleic acid can be immobilized (e.g., covalently or non-covalently). The bead can be, for example, composed of plastic, ceramic, metal, polymeric material, or any combination thereof. A bead can be, or comprise, a discrete particle that is spherical (e.g., microspheres) or have a non-spherical or irregular shape, such as cubic, cuboid, pyramidal, cylindrical, conical, oblong, or disc-shaped, and the like. In some embodiments, a bead can be non-spherical in shape.

Beads can comprise a variety of materials including, but not limited to, paramagnetic materials (e.g. magnesium, molybdenum, lithium, and tantalum), superparamagnetic materials (e.g. ferrite ($Fe_3O_4$; magnetite) nanoparticles), ferromagnetic materials (e.g. iron, nickel, cobalt, some alloys thereof, and some rare earth metal compounds), ceramic, plastic, glass, polystyrene, silica, methylstyrene, acrylic polymers, titanium, latex, sepharose, agarose, hydrogel, polymer, cellulose, nylon, and any combination thereof. In some embodiments, the bead (e.g., the bead to which the stochastic labels are attached) is a hydrogel bead. In some embodiments, the bead comprises hydrogel.

The size of the beads can vary. For example, the diameter of the bead can range from 0.1 micrometer to 50 micrometers. In some embodiments, the diameters of beads can be, or be about, 0.1, 0.5, 1, 2, 3, 4, 5, 6, 7, 8, 9, 10, 20, 30, 40, 50 micrometers, or a number or a range between any two of these values.

The diameters of the bead can be related to the diameter of the wells of the substrate. In some embodiments, the diameters of the bead can be, or be about, 10%, 20%, 30%, 40%, 50%, 60%, 70%, 80%, 90%, 100%, or a number or a range between any two of these values, longer or shorter than the diameter of the well. The diameter of the beads can be related to the diameter of a cell (e.g., a single cell entrapped by a well of the substrate). In some embodiments, the diameters of the beads can be, or be about, 10%, 20%, 30%, 40%, 50%, 60%, 70%, 80%, 90%, 100%, 150%, 200%, 250%, 300%, or a number or a range between any two of these values, longer or shorter than the diameter of the cell.

A bead can be attached to and/or embedded in a substrate. A bead can be attached to and/or embedded in a gel, hydrogel, polymer and/or matrix. The spatial position of a bead within a substrate (e.g., gel, matrix, scaffold, or polymer) can be identified using the spatial label present on the stochastic barcode on the bead which can serve as a location address.

Examples of beads can include, but are not limited to, streptavidin beads, agarose beads, magnetic beads, Dynabeads®, MACS® microbeads, antibody conjugated beads (e.g., anti-immunoglobulin microbeads), protein A conjugated beads, protein G conjugated beads, protein A/G conjugated beads, protein L conjugated beads, oligo(dT) conjugated beads, silica beads, silica-like beads, anti-biotin microbeads, anti-fluorochrome microbeads, and BcMag™ Carboxyl-Terminated Magnetic Beads.

A bead can be associated with (e.g. impregnated with) quantum dots or fluorescent dyes to make it fluorescent in one fluorescence optical channel or multiple optical channels. A bead can be associated with iron oxide or chromium oxide to make it paramagnetic or ferromagnetic. Beads can be identifiable. For example, a bead can be imaged using a camera. A bead can have a detectable code associated with the bead. For example, a bead can comprise a stochastic barcode. A bead can change size, for example due to swelling in an organic or inorganic solution. A bead can be hydrophobic. A bead can be hydrophilic. A bead can be biocompatible.

A solid support (e.g., bead) can be visualized. The solid support can comprise a visualizing tag (e.g., fluorescent dye). A solid support (e.g., bead) can be etched with an identifier (e.g., a number). The identifier can be visualized through imaging the beads.

Substrates and Microwell Arrays

As used herein, a substrate can refer to a type of solid support. A substrate can refer to a solid support that can comprise stochastic barcodes of the disclosure. A substrate can, for example, comprise a plurality of microwells. For example, a substrate can be a well array comprising two or more microwells. In some embodiments, a microwell can comprise a small reaction chamber of defined volume. In some embodiments, a microwell can entrap one or more cells. In some embodiments, a microwell can entrap only one cell. In some embodiments, a microwell can entrap one or more solid supports. In some embodiments, a microwell can entrap only one solid support. In some embodiments, a microwell entraps a single cell and a single solid support (e.g., bead). In some embodiments, a microwell can contain a single particle (e.g., a cell or a bead). In some embodiments, a microwell can contain two different particles (e.g., a cell and a bead).

Microwell Shapes

Microwells can be fabricated in a variety of shapes. Non-limiting exemplary well geometries can include cylindrical, conical, hemispherical, rectangular, or polyhedral (e.g., three dimensional geometries comprised of several planar faces, for example, hexagonal columns, octagonal columns, inverted triangular pyramids, inverted square pyramids, inverted pentagonal pyramids, inverted hexagonal pyramids, or inverted truncated pyramids). The microwells can comprise a shape that combines two or more of these geometries. For example, a microwell can be partly cylindrical, with the remainder having the shape of an inverted cone. A microwell can include two side-by-side cylinders, one of larger diameter (e.g. that corresponds roughly to the diameter of the beads) than the other (e.g. that corresponds roughly to the diameter of the cells), that are connected by a vertical channel (that is, parallel to the cylinder axes) that extends the full length (depth) of the cylinders. The location of the opening of the microwell can vary. For example, the opening of the microwell can be at the upper surface of the substrate. For example, the opening of the microwell can be at the lower surface of the substrate. The shape of the close end, for example the bottom, of the microwell can vary. For example, the closed end of the microwell can be flat. For example, the closed end of the microwell can have a curved surface (e.g., convex or concave). The shape and/or size of the microwell can be determined based on the types of cells or solid supports to be trapped within the microwells. In some embodiments, a microwell can have a non-circular cross section (e.g., square or hexagonal) in a plane of the substrate.

Microwell Sizes

Microwells can be fabricated in a variety of sizes. Microwell size can be characterized, for example, in terms of the diameter and/or the depth of the microwells. The diameter of the microwell can refer to the largest circle that can be inscribed within the planar cross-section of the microwell geometry. The diameter of the microwells can, in some embodiments, range from about 1-fold to about 10-folds the diameter of the cells or solid supports to be trapped within the microwells. In some embodiments, the microwell diameter can be, or be about, 1-fold, 1.5-fold, 2-folds, 3-folds, 4-folds, 5-folds, 6-folds, 7-folds, 8-folds, 9-files, 10-folds, or a number or a range between any two of these values, the diameter of the cells or the solid supports to be trapped within the microwells. In some embodiments, the microwell diameter can be at least, or at most, 1-fold, 1.5-fold, 2-folds, 3-folds, 4-folds, 5-folds, 6-folds, 7-folds, 8-folds, 9-files, 10-folds the diameter of the cells or the solid supports to be trapped within the microwells. In some embodiments, the microwell diameter can be about 2.5-folds the diameter of the cells or solid supports to be trapped within the microwells.

The diameter of a microwell can be specified in terms of absolute dimensions. The diameter of a microwell can range from about 1 nanometer to about 1000 micrometers. In some embodiments, the microwell diameter can be, or be about, 1, 2, 3, 4, 5, 6, 7, 8, 9, 10, 20, 30, 40, 50, 60, 70, 80, 90, 100, 200, 300, 400, 500, 600, 700, 800, 900, 1000 micrometers, or a number or a range between any two of these values. In some embodiments, the microwell diameter can be at least, or at most, 1, 2, 3, 4, 5, 6, 7, 8, 9, 10, 20, 30, 40, 50, 60, 70, 80, 90, 100, 200, 300, 400, 500, 600, 700, 800, 900, 1000 micrometers. In some embodiments, the microwell diameter can be, or be about, 1, 2, 3, 4, 5, 6, 7, 8, 9 10, 20, 30, 40, 50, 60, 70, 80, 90, 100, 200, 300, 400, 500, 600, 700, 800, 900, 1000 micrometers, or a number or a range between any two of these values. In some embodiments, the microwell diameter can be at least, or at most 1, 2, 3, 4, 5, 6, 7, 8, 9, 10, 20, 30, 40, 50, 60, 70, 80, 90, 100, 200, 300, 400, 500, 600, 700, 800, 900, 1000 micrometers. In some embodiments, the microwell diameter can be about 30 micrometers.

The depth of the microwell can vary, for example, to provide efficient trapping of droplets, for example cells and solid supports, or to provide efficient exchange of assay buffers and other reagents contained within the wells. The ratio of diameter to depth (i.e. aspect ratio) can be varied such that once a cell and/or a solid support settle inside a microwell, they will not be displaced by fluid motion above the microwell. In some embodiments, the depth of the microwell can be smaller than the diameter of the bead. For example, the depth of the microwell can be, or be about, 5%, 10%, 20%, 30%, 40%, 50%, 60%, 70%, 80%, 90%, 99%, 99.9%, 100%, or a number or a range between any two of these values, of the diameter of the bead. For example, the depth of the microwell can be at least, or at most, 5%, 10%, 20%, 30%, 40%, 50%, 60%, 70%, 80%, 90%, 99%, 99.9%, 100% of the diameter of the bead. In some embodiments, synthetic particles such as beads can protrude outside of the microwells.

In some embodiments, a dimension of a microwell allows the microwell to contain at most one bead. A ratio of the width of the microwell to a diameter of the bead can vary, ranging from 1-1.9. In some embodiments, the ratio of the width of the microwell to the diameter of the bead can be, or be about, 1, 1.1, 1.2, 1.3, 1.4, 1.5, 1.6, 1.7, 1.8, 1.9, or a number or a range between any two of these values. In some embodiments, the ratio of the width of the microwell to the diameter of the bead can be at least, or at most, 1, 1.1, 1.2, 1.3, 1.4, 1.5, 1.6, 1.7, 1.8, or 1.9.

The dimensions of a microwell can vary such that the microwell has sufficient space to accommodate a solid support and a cell of various sizes without being dislodged by fluid motion above the microwell. The depth of a microwell can range from about 1-fold to about 10-folds the diameter of the cells or solid supports to be trapped within the microwells. In some embodiments, the microwell depth can be, or be about, 1-fold, 1.5-fold, 2-folds, 3-folds, 4-folds, 5-folds, 6-folds, 7-folds, 8-folds, 9-files, 10-folds, or a number or a range between any two of these values, the diameter of the cells or solid supports to be trapped within the microwells. In some embodiments, the microwell depth can be at least, or at most, 1-fold, 1.5-fold, 2-folds, 3-folds, 4-folds, 5-folds, 6-folds, 7-folds, 8-folds, 9-files, or 10-folds the diameter of the cells or solid supports to be trapped within the microwells. In some embodiments, the microwell depth can be about 2.5-folds the diameter of the cells or solid supports to be trapped within the microwells.

An aspect ratio of the width of the microwell to the depth of the microwell can vary, for example ranging from 0.1-2. In some embodiments, the aspect ratio of the width of the microwell to the depth of the microwell can be, or be about, 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, or a number or a range between any two of these values. In some embodiments, the aspect ratio of the width of the microwell to the depth of the microwell can be at least, or at most, 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, or 2.

The depth of a microwell can be specified in terms of its absolute dimension. For example, the depth of a microwell can range from about 1 nanometer to about 1000 micrometers. In some embodiments, the microwell depth can be, or be about, 1, 2, 3, 4, 5, 6, 7, 8, 9, 10, 20, 30, 40, 50, 60, 70, 80, 90, 100, 200, 300, 400, 500, 600, 700, 800, 900, 1000 micrometers, or a number or a range between any two of these values. In some embodiments, the microwell depth can be at least, or at most, 1, 2, 3, 4, 5, 6, 7, 8, 9, 10, 20, 30, 40, 50, 60, 70, 80, 90, 100, 200, 300, 400, 500, 600, 700, 800, 900, 1000 micrometers. In some embodiments, the microwell depth can be, or be about, 1, 2, 3, 4, 5, 6, 7, 8, 9 10, 20, 30, 40, 50, 60, 70, 80, 90, 100, 200, 300, 400, 500, 600, 700, 800, 900, 1000 micrometers, or a number or a range between any two of these values. In some embodiments, the microwell depth can be at least, or at most, 1, 2, 3, 4, 5, 6, 7, 8, 9, 10, 20, 30, 40, 50, 60, 70, 80, 90, 100, 200, 300, 400, 500, 600, 700, 800, 900, 1000 micrometers. In some embodiments, the microwell depth can be about 30 micrometers.

The volume of a microwell can vary, for example ranging from about 1 picoliter to about 1000 microliters. In some embodiments, the microwell volume can be, or be about, 1, 2, 3, 4, 5, 6, 7, 8, 9, 10, 20, 30, 40, 50, 60, 70, 80, 90, 100, 200, 300, 400, 500, 600, 700, 800, 900, 1000, or a number or a range between any two of these values, picoliters. In some embodiments, the microwell volume can be at least, or at most, 1, 2, 3, 4, 5, 6, 7, 8, 9, 10, 20, 30, 40, 50, 60, 70, 80, 90, 100, 200, 300, 400, 500, 600, 700, 800, 900, or 1000 picoliters. In some embodiments, the microwell volume can be, or be about, 1, 2, 3, 4, 5, 6, 7, 8, 9, 10, 20, 30, 40, 50, 60, 70, 80, 90, 100, 200, 300, 400, 500, 600, 700, 800, 900, 1000, or a number or a range between any two of these values, nanoliters. In some embodiments, the microwell volume can be at least, or at most, 1, 2, 3, 4, 5, 6, 7, 8, 9, 10, 20, 30, 40, 50, 60, 70, 80, 90, 100, 200, 300, 400, 500, 600, 700, 800, 900, or 1000 nanoliters. In some embodiments, the microwell volume can be, or be about, 1, 2, 3, 4, 5, 6, 7, 8, 9, 10, 20, 30, 40, 50, 60, 70, 80, 90, 100, 200, 300, 400, 500, 600, 700, 800, 900, 1000, or a number or a range between any two of these values, microliters. In some embodiments, the microwell volume can be at least, or at most, 1, 2, 3, 4, 5, 6, 7, 8, 9, 10, 20, 30, 40, 50, 60, 70, 80, 90, 100, 200, 300, 400, 500, 600, 700, 800, 900, or 1000. In some embodiments, the microwell volume can be about 1 microliter.

The volume of a microwell can be characterized in terms of the variation in volume from one microwell to another. The coefficient of variation (expressed as a percentage) for microwell volume can range from about 1% to about 100%. The coefficient of variation for microwell volume can be, or be about, 1%, 2%, 3%, 4%, 5%, 6%, 7%, 8%, 9%, 10%, 20%, 30%, 40%, 50%, 60%, 70%, 80%, 90%, 100%, or a number or a range between any two of these values. The coefficient of variation for microwell volume can be, at least or at most, 1%, 2%, 3%, 4%, 5%, 6%, 7%, 8%, 9%, 10%, 20%, 30%, 40%, 50%, 60%, 70%, 80%, 90%, or 100%. In some embodiments, the coefficient of variation of microwell volume can be about 2.5%.

The ratio of the volume of a microwell to the surface area of a bead (or to the surface area of a solid support to which stochastic barcode oligonucleotides can be attached) can vary, for example range from about 2.5 to about 1520 micrometers. In some embodiments, the ratio can be, or be about, 2.5, 5, 10, 100, 500, 750, 1000, 1520 micrometers, or a number or a range between any two of these values. In some embodiments, the ratio can be at least, or at most, 2.5, 5, 10, 100, 500, 750, 1000, or 1520 micrometers. In some embodiments, the ratio can be about 67.5 micrometers.

Microwell Arrangements

Microwells can be arranged in a one dimensional, two dimensional, or three-dimensional array. A three dimensional array can be achieved, for example, by stacking a series of two or more two dimensional arrays, for example by stacking two or more substrates comprising microwell arrays.

The pattern and spacing between microwells can vary to optimize the efficiency of trapping a single cell and a single solid support (e.g., bead) in each well, as well as to maximize the number of wells per unit area of the array. The microwells can be distributed according to a variety of random or non-random patterns. For example, they can be distributed entirely randomly across the surface of the array substrate, or they can be arranged in a square grid, rectangular grid, hexagonal grid, or the like.

The center-to-center distance or the center-to-center spacing between wells can vary from about 1 micrometer to about 1000 micrometers. In some embodiments, the center-to-center distance between wells can be, or be about, 1, 2, 3, 4, 5, 6, 7, 8, 9, 10, 20, 30, 40, 50, 60, 70, 80, 90, 100, 200, 300, 400, 500, 600, 700, 800, 900, 1000 micrometers, or a number or a range between any two of these values. In some embodiments, the center-to-center distance between wells can be at least, or at most, 1, 2, 3, 4, 5, 6, 7, 8, 9, 10, 20, 30, 40, 50, 60, 70, 80, 90, 100, 200, 300, 400, 500, 600, 700, 800, 900, or 1000 micrometers. In some embodiments, the center-to-center distance between wells can be about 4890 micrometers.

The distance or the spacing between the edges of the microwells can vary from about 1 micrometer to about 1000 micrometers. In some embodiments, the distance between the edges of the wells can be, or be about, 1, 2, 3, 4, 5, 6, 7, 8, 9, 10, 20, 30, 40, 50, 60, 70, 80, 90, 100, 200, 300, 400, 500, 600, 700, 800, 900, 1000 micrometers, or a number or a range between any two of these values. In some embodiments, the distance between the edges of the wells can be at least, or at most, 1, 2, 3, 4, 5, 6, 7, 8, 9, 10, 20, 30, 40, 50, 60, 70, 80, 90, 100, 200, 300, 400, 500, 600, 700, 800, 900, or 1000 micrometers. In some embodiments, the distance between the edges of the wells can be about 80 micrometers.

Microwell Density

A microwell array can comprise microwells at varying densities, for example ranging from 100 microwells per $inch^2$ to 1000000 microwells per $inch^2$. In some embodiments, the density of the microwell array can be, or be about, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, 200000, 300000, 400000, 500000, 600000, 700000, 800000, 900000, 1000000, 2000000, 3000000, 4000000, 5000000, 6000000, 7000000, 8000000, 9000000, 10000000, or a number or a range between any two of these values, microwells per $inch^2$. In some embodiments, the density of the microwell array can be at least, or at most, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, 200000, 300000, 400000, 500000, 600000, 700000, 800000, 900000, 1000000, 2000000, 3000000, 4000000, 5000000, 6000000, 7000000, 8000000, 9000000, or 10000000 microwells per $inch^2$. In some embodiments, the density of the microwell array can be, or be about, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, or a number or a range between any two of these values, microwells per $cm^2$. In some embodiments, the density of the microwell array can be at least, or at most, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, or 100000 microwells per $cm^2$.

The total number of microwells on a substrate can vary based on the pattern and the spacing of the wells and the overall dimensions of the array. The number of microwells in the array can vary, for example, ranging from about 96 to about 1000000. In some embodiments, the number of microwells in the microarray can be, or be about, 96, 384, 1536, 2000, 3000, 4000, 5000, 6000, 7000, 8000, 9000, 10000, 20000, 30000, 40000, 50000, 60000, 70000, 80000, 90000, 100000, 200000, 300000, 400000, 500000, 600000, 700000, 800000, 900000, 1000000, 2000000, 3000000, 4000000, 5000000, 6000000, 7000000, 8000000, 9000000, 10000000, $10^8$, $10^9$, or a number or a range between any two of these values. In some embodiments, the number of microwells in the microarray can be at least, or at most, 96, 384, 1536, 2000, 3000, 4000, 5000, 6000, 7000, 8000, 9000, 10000, 20000, 30000, 40000, 50000, 60000, 70000, 80000, 90000, 100000 200000, 300000, 400000, 500000, 600000, 700000, 800000, 900000, 1000000, 2000000, 3000000, 4000000, 5000000, 6000000, 7000000, 8000000, 9000000, 10000000, $10^8$, $10^9$. In some embodiments, the number of microwells in the microwell array can be about 96. In some embodiments, the number of microwells can be about 150000.

Microwell Array Surface Features

A microwell array can comprise surface features between the microwells that are designed to help guide cells and solid supports into the wells and/or to prevent them from settling on the surfaces between wells. Non-limiting examples of suitable surface features include, but are not limited to, domed, ridged, or peaked surface features that encircle the wells or straddle the surface between wells.

Substrate Fabrication Techniques

A microwell can be fabricated using any of a number of fabrication techniques. Non-limiting examples of fabrication methods that can be used include bulk micromachining techniques such as photolithography and wet chemical etching, plasma etching, or deep reactive ion etching; micro-molding and micro-embossing; laser micromachining; 3D printing or other direct write fabrication processes using curable materials; and similar techniques.

Microwell arrays can be fabricated from a variety of substrate materials. The choice of material can depend on the choice of fabrication technique, and vice versa. Non-limiting examples of suitable materials include fused-silica, glass, polymers (e.g. agarose, gelatin, hydrogels, polydimethylsiloxane (PDMS) elastomer, polymethylmethacrylate (PMMA), polycarbonate (PC), polypropylene (PP), polyethylene (PE), high density polyethylene (HDPE), polyimide, cyclic olefin polymers (COP), cyclic olefin copolymers (COC), polyethylene terephthalate (PET), epoxy resins, thiol-ene based resins, metals or metal films (e.g. aluminum, stainless steel, copper, nickel, chromium, and titanium), and the like. A hydrophilic material can be desirable for fabrication of the microwell arrays (e.g. to enhance wettability and minimize non-specific binding of cells and other biological material). Hydrophobic materials that can be treated or coated (e.g. by oxygen plasma treatment, or grafting of a polyethylene oxide surface layer) can be used for fabrication of the microwell arrays. The use of porous, hydrophilic materials for the fabrication of the microwell array can be desirable in order to facilitate capillary wicking/venting of entrapped gas or air bubbles in the device. The microwell array can be fabricated from a single material. The microwell array can comprise two or more different materials that have been bonded together or mechanically joined.

Substrate Shapes and Sizes

A substrate can have variety of shapes and sizes. For example, the shape (or footprint) of the substrate within which microwells are fabricated can be square, rectangular, circular, or irregular in shape. The size of can be characterized by its width, length, and depth.

The width of a substrate can vary, ranging from 0.1 inch to 10 inches. In some embodiments, the width of the substrate can be, or be about, 0.1, 0.2, 0.3, 0.4, 05, 0.6, 0.7, 0.8, 0.9, 1, 2, 3, 4, 5, 6, 7, 8, 9, 10 inches, or a number or a range between any two of these values. In some embodiments, the width of the substrate can be at least, or at most, 0.1, 0.2, 0.3, 0.4, 05, 0.6, 0.7, 0.8, 0.9, 1, 2, 3, 4, 5, 6, 7, 8, 9, or 10 inches. The width of the substrate can vary, ranging from 0.2 centimeter to 20 centimeters. In some embodiments, the width of the substrate can be, or be about, 0.2, 0.2, 0.3, 0.4, 05, 0.6, 0.7, 0.8, 0.9, 1, 2, 3, 4, 5, 6, 7, 8, 9, 10, 20 centimeters, or a number or a range between any two of these values. In some embodiments, the width of the substrate can be at least, or at most, 0.2, 0.3, 0.4, 05, 0.6, 0.7, 0.8, 0.9, 1, 2, 3, 4, 5, 6, 7, 8, 9, 10, or 20 centimeters.

The length of a substrate can vary, ranging from 0.1 inch to 10 inches. In some embodiments, the length of the substrate can be, or be about, 0.1, 0.2, 0.3, 0.4, 05, 0.6, 0.7, 0.8, 0.9, 1, 2, 3, 4, 5, 6, 7, 8, 9, 10 inches, or a number or a range between any two of these values. In some embodiments, the length of the substrate can be at least, or at most, 0.1, 0.2, 0.3, 0.4, 05, 0.6, 0.7, 0.8, 0.9, 1, 2, 3, 4, 5, 6, 7, 8, 9, or 10 inches. The length of the substrate can vary, ranging from 0.2 centimeter to 20 centimeters. In some embodiments, the length of the substrate can be, or be about, 0.2, 0.2, 0.3, 0.4, 05, 0.6, 0.7, 0.8, 0.9, 1, 2, 3, 4, 5, 6, 7, 8, 9, 10, 20 centimeters, or a number or a range between any two of these values. In some embodiments, the length of the substrate can be at least, or at most, 0.2, 0.3, 0.4, 05, 0.6, 0.7, 0.8, 0.9, 1, 2, 3, 4, 5, 6, 7, 8, 9, 10, or 20 centimeters.

In some embodiments, the footprint of a substrate, for example defined by its width and length, can be similar to that of a microtiter plate. In some embodiments, the footprint of the microwell array substrate can be similar to that of standard microscope slides. Non-limiting examples of the footprint of standard microscope slides include about 75 mm long×25 mm wide (about 3" long× about 1" wide) and about 75 mm long×50 mm wide (about 3" long×2" wide).

The thickness of the substrate within which the microwells are fabricated can range from about 0.1 mm thick to about 10 mm thick, or more. The thickness of the microwell array substrate can be, or be about, 0.1, 0.5, 1, 2, 3, 4, 5, 6, 7, 8, 9, 10 mm, or a number or a range between any two of these values. The thickness of the microwell array substrate can be at least, or at most, 10, 9, 8, 7, 6, 5, 4, 3, 2, 1, 0.5, 0.1 mm. The thickness of the microwell array substrate can be about 1 mm thick. The thickness of the microwell array substrate can be any value within these ranges, for example, the thickness of the microwell array substrate can be between about 0.2 mm and about 9.5 mm.

Microwell Array Surface Treatments

A variety of surface treatments and surface modification techniques can be used to modify the properties of microwell array surfaces. Examples can include, but are not limited to, oxygen plasma treatments to render hydrophobic material surfaces more hydrophilic, the use of wet or dry etching techniques to smooth or roughen glass and silicon surfaces, adsorption or grafting of polyethylene oxide or other polymer layers, for example pluronic, or bovine serum albumin to substrate surfaces to render them more hydrophilic and less prone to non-specific adsorption of biomolecules and cells, the use of silane reactions to graft chemically-reactive functional groups to otherwise inert silicon and glass surfaces, etc. Photodeprotection techniques can be used to selectively activate chemically-reactive functional groups at specific locations in the array structure, for example, the selective addition or activation of chemically-reactive functional groups such as primary amines or carboxyl groups on the inner walls of the microwells can be used to covalently couple oligonucleotide probes, peptides, proteins, or other biomolecules to the walls of the microwells. The choice of surface treatment or surface modification utilized can depend on the type of surface property that is desired and/or on the type of material from which the microwell array is made.

Microwell Sealing

The openings of microwells can be sealed, for example, during cell lysis steps to prevent cross hybridization of target nucleic acid between adjacent microwells. A microwell (or array of microwells) can be sealed or capped using, for example, a flexible membrane or sheet of solid material (i.e. a plate or platten) that clamps against the surface of the microwell array substrate, or a suitable bead, where the diameter of the bead is larger than the diameter of the microwell.

A seal formed using a flexible membrane or sheet of solid material can comprise, for example, inorganic nanopore membranes (e.g., aluminum oxides), dialysis membranes, glass slides, coverslips, elastomeric films (e.g. PDMS), or hydrophilic polymer films (e.g., a polymer film coated with a thin film of agarose that has been hydrated with lysis buffer).

Solid supports (e.g., beads) used for capping the microwells can comprise any of the solid supports (e.g., beads) of the disclosure. In some embodiments, the solid supports are cross-linked dextran beads (e.g., Sephadex). Cross-linked dextran can range from about 10 micrometers to about 80 micrometers. In some embodiments, the cross-linked dextran beads used for capping can be, or be about, 10, 20, 30, 40, 50, 60, 70, 80 micrometers, or a number or a range between any two of these values. In some embodiments, the cross-linked dextran beads used for capping can be at least, or at most, 10, 20, 30, 40, 50, 60, 70, or 80 micrometers. The beads can be larger than the diameters of the microwells. In some embodiments, the beads can be, or be about, 10%, 20%, 30%, 40%, 50%, 60%, 70%, 80%, 90%, 99%, or a number or a range between any two of these values, larger than the diameter of the microwells. In some embodiments, the beads can be at least, or at most, 10%, 20%, 30%, 40%, 50%, 60%, 70%, 80%, 90%, or 99%, larger than the diameter of the microwells.

The seal or cap can allow buffer to pass into and out of the microwells, while preventing macromolecules (e.g., nucleic acids) from migrating out of the well. In some embodiments, a macromolecule of or of about 1, 2, 3, 4, 5, 6, 7, 8, 9, 10, 12, 13, 14, 15, 16, 17, 18, 19, 20, or a number or a range between any two of these values, nucleotides can be blocked from migrating into or out of the microwell by the seal or cap. In some embodiments, a macromolecule of at least, or at most, 1, 2, 3, 4, 5, 6, 7, 8, 9, 10, 12, 13, 14, 15, 16, 17, 18, 19, or 20 nucleotides can be blocked from migrating into or out of the microwell by the seal or cap.

Solid Support Manipulation

Solid supports (e.g., synthetic particles or beads) can be distributed among a substrate. Solid supports can be distributed among wells of the substrate, removed from the wells of the substrate, or otherwise transported through a device comprising one or more microwell arrays by means of centrifugation or other non-magnetic means. A microwell of a substrate can be pre-loaded with a solid support. A microwell of a substrate can hold or can hold about 1, 2, 3, 4, 5, 6, 7, 8, 9, 10 solid supports. A microwell of a substrate can hold at least, or at most, 1, 2, 3, 4, 5, 6, 7, 8, 9, 10 solid supports. In some embodiments, a microwell of a substrate can hold one solid support.

Consumables

Microwell arrays can be a consumable component of the assay system. Microwell arrays can be reusable. Microwell arrays can be configured for use as a stand-alone device for performing assays manually, or they can be configured to comprise a fixed or removable component of an instrument system that provides for full or partial automation of the assay procedure. In some embodiments of the disclosed methods, the bead-based libraries of stochastic barcodes can be deposited in the wells of the microwell array as part of the assay procedure. In some embodiments, the beads can be pre-loaded into the wells of the microwell array and provided to the user as part of, for example, a kit for performing stochastic barcoding and digital counting of nucleic acid targets.

Two Mated Microwell Arrays

In some embodiments, two mated microwell arrays can be provided, one pre-loaded with beads which are held in place by a first magnet, and the other for use by the user in loading individual cells. Following distribution of cells into the second microwell array, the two arrays can be placed face-to-face and the first magnet removed while a second magnet is used to draw the beads from the first array down into the corresponding microwells of the second array, thereby ensuring that the beads rest above the cells in the second microwell array and thus minimizing diffusional loss of target molecules following cell lysis, while maximizing efficient attachment of target molecules to the stochastic barcodes on the bead.

Substrates without Microwells

In some embodiments, a substrate does not include microwells. For example, beads can be assembled. For example, beads can be self-assembled. The beads can self-assemble into a monolayer. The monolayer can be on a flat surface of the substrate. The monolayer can be on a curved surface of the substrate. The bead monolayer can be formed by any method, such as alcohol evaporation.

Individual cells and beads can be compartmentalized using alternatives to microwells, for example, a single solid support and a single cell could be confined within a single droplet in an emulsion (e.g. in a droplet digital microfluidic system).

Cells could be confined within porous beads that themselves comprise the plurality of tethered stochastic barcodes. Individual cells and solid supports can be compartmentalized in any type of container, microcontainer, reaction chamber, reaction vessel, or the like.

Single cell, stochastic barcoding can be performed without the use of microwells. Single cell, stochastic barcoding assays can be performed without the use of any physical container. For example, stochastic barcoding without a physical container can be performed by embedding cells and beads in close proximity to each other within a polymer layer or gel layer to create a diffusional barrier between different cell/bead pairs. For example, stochastic barcoding without a physical container can be performed in situ, in vivo, on an intact solid tissue, on an intact cell, and/or subcellularly.

Methods of Stochastic Barcoding

Provided herein are methods for estimating the number of distinct targets at distinct locations in a physical sample (e.g., tissue, organ, tumor, cell). The methods can comprise placing the stochastic barcodes in close proximity with the sample, lysing the sample, associating distinct targets with the stochastic barcodes, amplifying the targets and/or digitally counting the targets. The method can further comprise analyzing and/or visualizing the information obtained from the spatial labels on the stochastic barcodes. In some embodiments, the method comprises visualizing the plurality of targets in the sample. Mapping the plurality of targets onto the map of the sample can include generating a two dimensional map or a three dimensional map of the sample. The two dimensional map and the three dimensional map can be generated prior to or after stochastically barcoding the plurality of targets in the sample. Visualizing the plurality of targets in the sample can include mapping the plurality of targets onto a map of the sample. Mapping the plurality of targets onto the map of the sample can include generating a two dimensional map or a three dimensional map of the sample. The two dimensional map and the three dimensional map can be generated prior to or after stochastically barcoding the plurality of targets in the sample. In some embodiments, the two dimensional map and the three dimensional map can be generated before or after lysing the sample. Lysing the sample before or after generating the two dimensional map or the three dimensional map can include heating the sample, contacting the sample with a detergent, changing the pH of the sample, or any combination thereof.

In some embodiments, stochastically barcoding the plurality of targets comprises hybridizing a plurality of stochastic barcodes with a plurality of targets to create stochastically barcoded targets. Stochastically barcoding the plurality of targets can comprise generating an indexed library of the stochastically barcoded targets. Generating an indexed library of the stochastically barcoded targets can be performed with a solid support comprising the plurality of stochastic barcodes.

Contacting a Sample and Stochastic Barcode(s)

The disclosure provides for methods for contacting a sample (e.g., cells) to a substrate of the disclosure. A sample comprising, for example, a cell, organ, or tissue thin section, can be contacted to stochastic barcodes. The cells can be contacted, for example, by gravity flow wherein the cells can settle and create a monolayer. The sample can be a tissue thin section. The thin section can be placed on the substrate. The sample can be one-dimensional (e.g., form a planar surface). The sample (e.g., cells) can be spread across the substrate, for example, by growing/culturing the cells on the substrate.

When stochastic barcodes are in close proximity to targets, the targets can hybridize to the stochastic barcode. The stochastic barcodes can be contacted at a non-depletable ratio such that each distinct target can associate with a distinct stochastic barcode of the disclosure. To ensure efficient association between the target and the stochastic barcode, the targets can be crosslinked to the stochastic barcode.

Cell Lysis

Following the distribution of cells and stochastic barcodes, the cells can be lysed to liberate the target molecules. Cell lysis can be accomplished by any of a variety of means, for example, by chemical or biochemical means, by osmotic shock, or by means of thermal lysis, mechanical lysis, or optical lysis. Cells can be lysed by addition of a cell lysis buffer comprising a detergent (e.g. SDS, Li dodecyl sulfate, Triton X-100, Tween-20, or NP-40), an organic solvent (e.g. methanol or acetone), or digestive enzymes (e.g. proteinase K, pepsin, or trypsin), or any combination thereof. To increase the association of a target and a stochastic barcode, the rate of the diffusion of the target molecules can be altered by for example, reducing the temperature and/or increasing the viscosity of the lysate.

In some embodiments, the sample can be lysed using a filter paper. The filter paper can be soaked with a lysis buffer on top of the filter paper. The filter paper can be applied to the sample with pressure which can facilitate lysis of the sample and hybridization of the targets of the sample to the substrate.

In some embodiments, lysis can be performed by mechanical lysis, heat lysis, optical lysis, and/or chemical lysis. Chemical lysis can include the use of digestive enzymes such as proteinase K, pepsin, and trypsin. Lysis can be performed by the addition of a lysis buffer to the substrate. A lysis buffer can comprise Tris HCl. A lysis buffer can comprise at least about 0.01, 0.05, 0.1, 0.5, or 1 M or more Tris HCl. A lysis buffer can comprise at most about 0.01, 0.05, 0.1, 0.5, or 1 M or more Tris HCL. A lysis buffer can comprise about 0.1 M Tris HCl. The pH of the lysis buffer can be at least about 1, 2, 3, 4, 5, 6, 7, 8, 9, or 10 or more. The pH of the lysis buffer can be at most about 1, 2, 3, 4, 5, 6, 7, 8, 9, or 10 or more. In some embodiments, the pH of the lysis buffer is about 7.5. The lysis buffer can comprise a salt (e.g., LiCl). The concentration of salt in the lysis buffer can be at least about 0.1, 0.5, or 1 M or more. The concentration of salt in the lysis buffer can be at most about 0.1, 0.5, or 1 M or more. In some embodiments, the concentration of salt in the lysis buffer is about 0.5M. The lysis buffer can comprise a detergent (e.g., SDS, Li dodecyl sufate, triton X, tween, NP-40). The concentration of the detergent in the lysis buffer can be at least about 0.0001%, 0.0005%, 0.001%, 0.005%, 0.01%, 0.05%, 0.1%, 0.5%, 1%, 2%, 3%, 4%, 5%, 6%, or 7% or more. The concentration of the detergent in the lysis buffer can be at most about 0.0001%, 0.0005%, 0.001%, 0.005%, 0.01%, 0.05%, 0.1%, 0.5%, 1%, 2%, 3%, 4%, 5%, 6%, or 7% or more. In some embodiments, the concentration of the detergent in the lysis buffer is about 1% Li dodecyl sulfate. The time used in the method for lysis can be dependent on the amount of detergent used. In some embodiments, the more detergent used, the less time needed for lysis. The lysis buffer can comprise a chelating agent (e.g., EDTA, EGTA). The concentration of a chelating agent in the lysis buffer can be at least about 1, 5, 10, 15, 20, 25, or 30 mM or more. The concentration of a chelating agent in the lysis buffer can be at most about 1, 5, 10, 15, 20, 25, or 30 mM or more. In some embodiments, the concentration of chelating agent in the lysis buffer is about 10 mM. The lysis buffer can comprise a reducing reagent (e.g., beta-mercaptoethanol, DTT). The concentration of the reducing reagent in the lysis buffer can be at least about 1, 5, 10, 15, or 20 mM or more. The concentration of the reducing reagent in the lysis buffer can be at most about 1, 5, 10, 15, or 20 mM or more. In some embodiments, the concentration of reducing reagent in the lysis buffer is about 5 mM. In some embodiments, a lysis buffer can comprise about 0.1M TrisHCl, about pH 7.5, about 0.5M LiCl, about 1% lithium dodecyl sulfate, about 10 mM EDTA, and about 5 mM DTT.

Lysis can be performed at a temperature of about 4, 10, 15, 20, 25, or 30° C. Lysis can be performed for about 1, 5, 10, 15, or 20 or more minutes. A lysed cell can comprise at least about 100000, 200000, 300000, 400000, 500000, 600000, or 700000 or more target nucleic acid molecules. A lysed cell can comprise at most about 100000, 200000, 300000, 400000, 500000, 600000, or 700000 or more target nucleic acid molecules.

Attachment of Stochastic Barcodes to Target Nucleic Acid Molecules

Following lysis of the cells and release of nucleic acid molecules therefrom, the nucleic acid molecules can randomly associate with the stochastic barcodes of the co-localized solid support. Association can comprise hybridization of a stochastic barcode's target recognition region to a complementary portion of the target nucleic acid molecule (e.g., oligo(dT) of the stochastic barcode can interact with a poly(A) tail of a target). The assay conditions used for hybridization (e.g. buffer pH, ionic strength, temperature, etc.) can be chosen to promote formation of specific, stable hybrids. In some embodiments, the nucleic acid molecules released from the lysed cells can associate with the plurality of probes on the substrate (e.g., hybridize with the probes on the substrate). When the probes comprise oligo(dT), mRNA molecules can hybridize to the probes and be reverse transcribed. The oligo(dT) portion of the oligonucleotide can act as a primer for first strand synthesis of the cDNA molecule. For example, mRNA molecules can hybridize to stochastic barcodes on beads. For example, single-stranded nucleotide fragments can hybridize to the target-binding regions of stochastic barcodes.

Attachment can further comprise ligation of a stochastic barcode's target recognition region and a portion of the target nucleic acid molecule. For example, the target binding region can comprise a nucleic acid sequence that can be capable of specific hybridization to a restriction site overhang (e.g. an EcoRI sticky-end overhang). The assay procedure can further comprise treating the target nucleic acids with a restriction enzyme (e.g. EcoRI) to create a restriction site overhang. The stochastic barcode can then be ligated to any nucleic acid molecule comprising a sequence complementary to the restriction site overhang. A ligase (e.g., T4 DNA ligase) can be used to join the two fragments.

For example, the labeled targets from a plurality of cells (or a plurality of samples) (e.g., target-barcode molecules) can be subsequently pooled, for example, into a tube. The labeled targets can be pooled by, for example, retrieving the stochastic barcodes and/or the beads to which the target-barcode molecules are attached.

The retrieval of solid support-based collections of attached target-barcode molecules can be implemented by use of magnetic beads and an externally-applied magnetic field. Once the target-barcode molecules have been pooled, all further processing can proceed in a single reaction vessel. Further processing can include, for example, reverse transcription reactions, amplification reactions, cleavage reactions, dissociation reactions, and/or nucleic acid extension reactions. Further processing reactions can be performed within the microwells, that is, without first pooling the labeled target nucleic acid molecules from a plurality of cells.

Loading Station

The disclosure provides for loading stations for facilitating performance of one or more workflow procedures using a flowcell and/or microwell array. For example, the loading systems described herein can be used to facilitate stochastic barcoding.

A non-limiting embodiment of a loading station 100 is illustrated in FIG. 1. The loading station 100 can include one or more structures or features designed to facilitate performance of a workflow. In some embodiments, a workflow can include a series of steps for hybridizing genetic information from a plurality of cells onto a plurality of barcode-bearing beads. For example, in some embodiments, a workflow can include steps of introducing a plurality of cells into a microcell array, introducing a plurality of barcode-bearing beads into the microwell array, lysing the plurality of cells so that genetic information from the cells hybridizes with the plurality of beads, and/or collecting the beads from the microwell array.

As described herein, the microwell array for use with the flowcell 100 can include one or more microwells. Each microwell can be configured to receive one or more particles, such as barcode-bearing beads and/or cells. In some embodiments, the microwell array can be packaged within a flowcell that provides for convenient interfacing with the loading station 100 and facilitates the exchange of fluids, e.g. cell and solid support suspensions, lysis buffers, rinse buffers, etc., that are delivered to the microwell array. In some embodiments, the microwell array and the flowcell can be packaged within a consumable cartridge that provides for convenient interfacing with loading station 100.

As shown in FIG. 1, the loading station 100 includes a body 105 and a tray 110. The tray 110 can be positioned on a superior surface of the body 105. In some embodiments, the tray 110 can receive a microwell array, flowcell, and/or cartridge within the loading station 100. In some embodiments, the tray 110 can be dimensioned, positioned, or otherwise configured to orient a microwell array, flowcell, and/or cartridge in a predefined position within the loading station 100. The predefined position can facilitate the interaction of other features of the loading station 100 with the microwell array, flowcell, and/or cartridge. In some embodiments, the tray 110 can releasably secure the microwell array, flowcell, and/or cartridge within the loading station 100. Securing the microwell array, flowcell, and/or cartridge within the loading station 100 can prevent misalignment of the microwell array, flowcell, and/or cartridge with other features of the loading station 100 while a workflow is performed using the loading station 100.

In some embodiments, the loading station 100 can include a magnet 120. The magnet 120 can be positioned adjacent to the tray 110. In some embodiments, the magnet 120 can be positioned inferior to at least a portion of the tray 110 and/or the microwell array when positioned within the loading station 100. In some embodiments, the tray 110 can include a cover 114 positioned between the magnet 120 and a location of the tray 110 for receiving the microwell array, flowcell, and/or cartridge. In such embodiments, the cover 114 can restrict spillover or other contamination from the microwell array, flowcell, and/or cartridge from reaching the magnet 120. In some embodiments, the magnet 120 can be positioned within the body 105 of the loading station 100. In some embodiments, the magnet 120 can be configured to produce a magnetic field to attract one or more particles within the microwell array. For example, in some embodiments, one or more barcode-bearing beads can be magnetic or can have a magnetic material affixed thereon. In some embodiments, the magnet 120 can be configured to attract the barcode-bearing beads.

In some embodiments, the magnet 120 can be movable relative to the tray 110 and/or microwell array when positioned within the tray 110. For example, in some embodiments the magnet 120 can be movable between a first position or inactive position in which a magnetic field produced by the magnet 120 does not attract magnetic particles within the microwell array or exerts a relatively weak attractive force on magnetic particles positioned within the microwell array when the microwell array is positioned within the tray 110 and a second position or active position in which the magnetic field produced by the magnet 120 can attract magnetic particles within the microwell array when the microwell array is positioned within the tray 110.

When in the active position a superior surface of the magnet 120 can be in parallel with an inferior surface of the flowcell and/or cartridge. In some embodiments, the superior surface of the magnet 120 can be 1.0 mm away or approximately 1.0 mm away from the inferior surface of the flowcell and/or cartridge when in the active position. In some embodiments, the superior surface of the magnet 120 can be 0.5 mm, 1.5 mm, 2.0 mm, 2.5 mm, 3.0 mm, less than 0.5 mm, less than 1.0 mm, no more than 1.0 mm, less than 1.5 mm, less than 2.0 mm, less than 2.5 mm, less than 3.0 mm, or between 0.5 mm and 1.5 mm away from the inferior surface of the flowcell and/or cartridge when the magnet 120 is in the active position. In some embodiments, the superior surface of the magnet 120 can be sized and shaped to extend to or beyond the boundaries of an active area of the flowcell.

In some embodiments, in the inactive position, at least a portion of the magnet 120 is positioned at a further distance from the microwell array in at least one direction in comparison to the active position. The magnet 120 is shown in the inactive position in FIG. 1.

Although two positions of the magnet 120 are described with respect to FIG. 1, it should be recognized that in certain embodiments, the magnet 120 can move over more than two positions. In some embodiments, the magnet 120 can move between discrete positions. In some embodiments, the magnet 120 can move over a continuous range of positions. Different positions of the magnet 120 can allow for the application of different amounts of magnetic force on magnetic particles within the microarray when the microarray is positioned within the tray 110.

In some embodiments, the loading station 100 can include a magnet 130. The magnet 130 can be positioned adjacent to the tray 110. In some embodiments, the magnet 130 can be positioned superior to at least a portion of the tray 110 and/or the microwell array when positioned within the loading station 100. In some embodiments, the magnet 130 can be positioned within a portion of the body 105. In some embodiments, the magnet 130 can be configured to produce a magnetic field to attract one or more particles within the microwell array, such as, for example, the barcode-bearing beads.

In some embodiments the magnet 130 can be movable between a first position or inactive position in which a magnetic field produced by the magnet 130 does not attract magnetic particles within the microwell array or exerts a relatively weak attractive force on magnetic particles positioned within the microwell array when the microwell array is positioned within the tray 110 and a second position or active position in which the magnetic field produced by the magnet 130 can attract magnetic particles within the microwell array when the microwell array is positioned within the tray 110.

When in the active position an inferior surface of the magnet 130 can be in parallel with a superior surface of the flowcell and/or cartridge. In some embodiments, the inferior surface of the magnet 130 can be 1.0 mm away or approximately 1.0 mm away from the superior surface of the flowcell and/or cartridge when in the active position. In some embodiments, the inferior surface of the magnet 130 can be 0.5 mm, 1.5 mm, 2.0 mm, 2.5 mm, 3.0 mm, less than 0.5 mm, less than 1.0 mm, no more than 1.0 mm, less than 1.5 mm, less than 2.0 mm, less than 2.5 mm, less than 3.0 mm, or between 0.5 mm and 1.5 mm away from the superior surface of the flowcell and/or cartridge when the magnet 130 is in the active position. In some embodiments, the inferior surface of the magnet 130 can be sized and shaped to extend to or beyond the boundaries of the active area of the flowcell.

The magnet 130 is shown in the inactive position in FIG. 1. In some embodiments, the magnet 130 is positioned within the body 105 of the loading station 100 when in the first position. In some embodiments, the magnet 130 extends out of an opening 107 in the housing 105 when transitioning to the active position.

Although two positions of the magnet 130 are described with respect to FIG. 1, it should be recognized that in certain embodiments, the magnet 130 can move over more than two positions. In some embodiments, the magnet 130 can move between discrete positions. In some embodiments, the magnet 130 can move over a continuous range of positions. Different positions of the magnet 130 can allow for the application of different amounts of magnetic force on magnetic particles within the microarray when the microarray is positioned within the tray 110.

In some embodiments, the loading station 100 can include an actuator 140. In some embodiments, the actuator 140 can be actuated to transition the magnet 120 between the inactive position and the active position. In some embodiments, the actuator 140 can be actuated to transition the magnet 130 between the inactive position and the active position. In some embodiments, the actuator 120 can be actuated to move either the magnet 120 or the magnet 130 between their respective inactive positions and active positions. In some embodiments, the actuator 140 can be actuated to move both the magnet 120 and the magnet 130 between their respective inactive positions and active positions.

In some embodiments, the loading station 100 can be configured to prevent both the magnet 120 and magnet 130 from being positioned within their respective active positions at the same time. For example, in some embodiments, the magnet 120 and magnet 130 are mechanically coupled such that movement of the magnet 120 to its active position causes movement of the magnet 130 to its inactive position. In some embodiments, movement of the magnet 130 to its active position causes movement of the magnet 120 to its inactive position. In some embodiments, both the magnet 120 and the magnet 130 can be mechanically coupled to the actuator 140 such that movement of the actuator 140 in a direction that causes the magnet 120 to transition to its active position results in movement of the magnet 130 from its active position to its inactive position or results in maintenance of the magnet 130 in its inactive position. In some embodiments, movement of the actuator in a direction that causes the magnet 130 to transition to its active position results in movement of the magnet 120 from its active position to its inactive position or results in maintenance of the magnet 120 in its inactive position. In some embodiments, the actuator 140 can be part of an actuation mechanism in which the actuator 140 is configured to engage one more actuation components mechanically coupled to the magnet 120 in certain positions and one or more actuation components mechanically coupled to the magnet 130 in other positions.

In some embodiments, the actuator 140 can be moved between three positions, a first position, a second position, and a third position. In some embodiments, when the actuator is in the first position, both the magnet 120 and the magnet 130 are in their respective inactive positions. The first position of the actuator can be referred to as a "neutral" position. In some embodiments, transitioning the actuator 140 to its second position can cause the magnet 120 to transition to its active position. The second position of the actuator can be referred to as a "lysis" position. As described further herein, in certain embodiments, positioning the magnet 120 in its active position can facilitate lysis of cells within the microwell array when the microwell array is positioned within the tray 110. In some embodiments, the actuator 140 is mechanically coupled to the magnet 120 and 130 such that the magnet 130 is positioned within its inactive position when the actuator is in the second position. In some embodiments, transitioning the actuator 140 to its third position can cause the magnet 130 to transition to its active position. The third position of the actuator can be referred to as a "retrieval" position. As described further herein, in certain embodiments, positioning the magnet 130 in its active position can facilitate retrieval of barcode-bearing beads positioned within the microwell array when the microwell array is positioned within the tray 110.

Although three positions of the actuator 140 are described with respect to FIG. 1, it should be recognized that in certain embodiments, the actuator 140 can move between two positions or between more than two positions. In some embodiments, the actuator 140 can move between discrete positions. In some embodiments, the actuator 140 can move over a continuous range of positions.

As shown in FIG. 1, the actuator 140 can be a sliding actuator configured to slide along a track. In some embodiments, the actuator 140 can be a lever, a button, a switch, or any other suitable actuator.

In some embodiments, the loading station 100 can include drawer 150. In some embodiments, the drawer 150 can include a receptacle 156. The receptacle 156 can be configured to receive one or more tubes. FIG. 1 depicts a first tube 152*a* and a second tube 152*b* positioned within the tube receptacle 156 of the drawer 150. In some embodiments, the tubes 152*a* and 152*b* are Eppendorf tubes. In some embodiments, the tubes 152*a* and 152*b* are 5 ml Eppendorf tubes.

In some embodiments, the drawer 150 can position the tubes 152*a* and 152*b* within the loading station 100. For example, the drawer 150 can align at least one of the tubes 152*a* and 152*b* with an outlet of the flowcell containing the microwell array.

In some embodiments, the drawer 150 is movable within the load cell 100. In some embodiments, the drawer 150 is movable to a first position, in which a portion of the drawer 150 is positioned outside of the body 105. In some embodiments, the first position can be a loading position. When in the loading position, tubes 152*a* and 152*b* can be received by the receptacle 156 of the drawer 150 and/or removed from the drawer 150.

In some embodiments, the drawer 150 is movable to a second position. In the second position, the drawer 150 can be positioned within the body 105. In some embodiments, one of the tubes 152*a* and 152*b* are aligned with the outlet of the flowcell when the drawer 150 is in the second position. In some embodiments, the second position is a waste collection position, in which one of the tubes 152*a* and 152*b* designated for waste collection is aligned with the outlet of the flowcell.

In some embodiments, the drawer 150 is moveable to a third position. In the third position, the drawer 150 can be positioned within the body 105. In some embodiments, the one of the tubes 152*a* and 152*b* that does not align with the outlet of the flowcell in the second position can be aligned with the outlet of the flowcell in the third position. In some embodiments, the third position is a bead collection position, in which one of the tubes 152a and 152b designated for bead collection is aligned with the outlet of the flowcell.

In some embodiments, the drawer 150 can be movable along a guiderail. In some embodiments, the guiderail should be positioned to engage a top surface of the drawer 150 or side surface of the drawer 150 in use. In some embodiments, the guiderail should be positioned to reduce contact from spilling or splashing liquids within the collection tubes 152a and 152b. In some embodiments, the drawer 150 can be positioned within a separate compartment of the body 105 from the magnet 120 and/or the magnet 130 to prevent contact from spilling or splashing liquids within the collection tubes. In some embodiments, the drawer 150 can be positioned such that motion of the drawer 150 does not interfere with motion of the magnet 120.

In some embodiments, the loading station 100 can include an actuator 160. In some embodiments, the actuator 160 can be mechanically coupled to the drawer 150. In some embodiments, the actuator 160 can be actuated to transition the drawer 150 between the first position, the second position, and/or the third position of the drawer 150 by movement of the actuator 160 between a first position, a second position, and a third position, respectively.

Although three positions of the actuator 160 are described with respect to FIG. 1, it should be recognized that in certain embodiments, the actuator 160 can move between two positions or between more than two positions. In some embodiments, the actuator 160 can move between discrete positions. In some embodiments, the actuator 160 can move over a continuous range of positions.

As shown in FIG. 1, the actuator 160 can be a sliding actuator configured to slide along a track. In some embodiments, the actuator 160 can be a lever, a button, a switch, or any other suitable actuator.

As described herein, the body 105 can provide a housing for various components of the loading station 100. In some embodiments, the body 105 can provide a housing to prevent damage to components of the loading system, such as the magnet 120 and the magnet 130. In some embodiments, the body 105 can house the magnets 120 and 130 in order to prevent magnetic attraction of external bodies.

In some embodiments, the loading station 100 can be dimensioned so that the loading station 100 can be portable. In some embodiments, the loading station 100 can be light weight. In some embodiments, components of the loading station can be formed of materials that facilitate sterilization using alcohol wipes and/or bleach. In some embodiments, components of the loading station can be formed of materials that facilitate sterilization using alcohol wipes and 10% bleach.

Although the embodiment of the loading station 100 shown in FIG. 1 includes two magnets, in certain embodiments, the loading station 100 may include only a single magnet configured to move over a range of positions. For example, in some embodiments, the single magnet can be movable to the active position of the magnet 120 for certain steps in a workflow performed using the loading station 100. In some embodiments, the single magnet can be movable to the active position of magnet 130 during other steps in the workflow performed using the loading station 100. In certain embodiments, the single magnet can be moved to one or more other positions in which the single magnet does not exert a force or exerts a relatively weak force on the beads during other steps in the workflow performed using the loading station 100, such as, for example, the inactive position of the magnet 120 and/or the inactive position of the magnet 130.

In some embodiments, the loading station 100 can have more than two magnets. In some embodiments, each magnet can have a separate actuator for transitioning between its inactive position and active position.

Flow Cell

As discussed herein, in some embodiments, the microwell array can be positioned within a flowcell to facilitate interfacing with the loading station 100. Design features can include: (i) one or more inlet ports for introducing cell samples, solid support suspensions, or other assay reagents, (ii) one or more microwell array chambers designed to provide for efficient (e.g., uniform) filling and fluid-exchange while minimizing back eddies or dead zones, and (iii) one or more outlet ports for delivery of fluids to a sample collection point or a waste reservoir.

The design of the flowcell can include a plurality of microarray chambers that interface with a plurality of microwell arrays such that one or more different cell samples can be processed in parallel. The design of the flowcell can further include features for creating consistent (e.g., uniform) flow velocity profiles, i.e. "plug flow", across the width of the array chamber to provide for more efficient (e.g., uniform) delivery of cells and beads to the microwells, for example, by using a porous barrier located near the chamber inlet and upstream of the microwell array as a "flow diffuser", or by dividing each array chamber into several subsections that collectively cover the same total array area, but through which the divided inlet fluid stream flows in parallel. In some embodiments, the flowcell can enclose or incorporate more than one microwell array substrate. In some embodiments, the integrated microwell array/flowcell assembly can constitute a fixed component of the system. In some embodiments, the microwell array/flowcell assembly can be removable from the instrument.

In general, the dimensions of fluidic channel(s) and the array chamber(s) in flowcell designs will be optimized to (i) provide efficient (e.g., uniform) delivery of cells and beads to the microwell array, and (ii) to minimize sample and reagent consumption. The width of a fluidic channel can be different in different implementations, for example, ranging from 0.1 mm to 100 mm. In some embodiments, the width can be, or be about, 0.1, 0.2, 0.3, 0.4, 0.5, 0.6, 0.7, 0.8, 0.9, 1, 2, 3, 4, 5, 6, 7, 8, 9, 10, 20, 30, 40, 50, 60, 70, 80, 90, 100 mm, or a number or a range between any two of these values. In some embodiments, the width can be at least, or at most, 0.1, 0.2, 0.3, 0.4, 0.5, 0.6, 0.7, 0.8, 0.9, 1, 2, 3, 4, 5, 6, 7, 8, 9, 10, 20, 30, 40, 50, 60, 70, 80, 90, or 100 mm.

The height of a fluidic channel can be different in different implementations, for example, ranging from 0.1 mm to 100 mm. In some embodiments, the height can be, or be about, 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 3, 4, 5, 6, 7, 8, 9, 10 mm, or a number or a range between any two of these values. In some embodiments, the height can be at least, or at most, 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 3, 4, 5, 6, 7, 8, 9, or 10 mm.

Flowcells can be fabricated using a variety of techniques and materials known to those of skill in the art. In general, a flowcell can be fabricated as a separate part and subsequently either mechanically clamped or permanently bonded to the microwell array substrate. Examples of suitable fabrication techniques include conventional machining, CNC machining, injection molding, 3D printing, alignment and lamination of one or more layers of laser or die-cut polymer films, or any of a number of microfabrication techniques such as photolithography and wet chemical etching, dry etching, deep reactive ion etching, or laser micromachining.

Once the flowcell part has been fabricated it can be attached to the microwell array substrate mechanically, e.g. by clamping it against the microwell array substrate (with or without the use of a gasket), or it can be bonded directly to the microwell array substrate using any of a variety of techniques (depending on the choice of materials used) known to those of skill in the art, for example, through the use of anodic bonding, thermal bonding, or any of a variety of adhesives or adhesive films, including epoxy-based, acrylic-based, silicone-based, UV curable, polyurethane-based, or cyanoacrylate-based adhesives. In some embodiments, the substrate can form the fluidic channel bottom of the fluidic channel, or the substrate can be on the fluidic channel bottom of the fluidic channel. In some embodiments, the substrate comprises silicon, fused-silica, glass, a polymer, a metal, an elastomer, polydimethylsiloxane, agarose, a hydrogel, or a combination thereof.

Flowcells can be fabricated using a variety of materials known to those of skill in the art. In general, the choice of material used will depend on the choice of fabrication technique used, and vice versa. Examples of suitable materials include, but are not limited to, silicon, fused-silica, glass, any of a variety of polymers, e.g. polydimethylsiloxane (PDMS; elastomer), polymethylmethacrylate (PMMA), polycarbonate (PC), polypropylene (PP), polyethylene (PE), high density polyethylene (HDPE), polyimide, cyclic olefin polymers (COP), cyclic olefin copolymers (COC), polyethylene terephthalate (PET), epoxy resins, metals (e.g. aluminum, stainless steel, copper, nickel, chromium, and titanium), a non-stick material such as teflon (PTFE), or a combination of these materials. The cyclic olefin polymers (COP) can comprise Zeonor 1020R or Zeonor 1060R.

Cartridge

As described herein, the microwell array and the flowcell, can be packaged within a consumable cartridge that provides for convenient interfacing with the rest of the loading station 100. The flowcell can facilitate the exchange of fluids, e.g. cell and bead suspensions, lysis buffers, rinse buffers, etc., that are delivered to the microwells. In some embodiments, the flow cell may be designed to facilitate efficient (e.g., uniform) distribution of cells and beads across the plurality of microwells. Design features may include: (i) one or more inlet ports for introducing cell samples, bead suspensions, or other assay reagents, (ii) one or more microwell chambers designed to provide for efficient (e.g., uniform) filling and efficient fluid-exchange while minimizing back eddies or dead zones, and (iii) one or more outlet ports for delivery of fluids to a sample collection point or a waste reservoir. In some embodiments, the design of the flow cell may include a plurality of microwell chambers that interface with a plurality of microwell arrays on a single substrate, or with a plurality of microwell array substrates, such that one or more different cell samples may be processed in parallel. In some embodiments, the design of the flow cell, e.g. the layout of the fluid channels and chambers, may be adjusted so that different patterns of microwells (i.e. configurable microarray patterns) are accessed by fluids in a given design.

Figure 2:
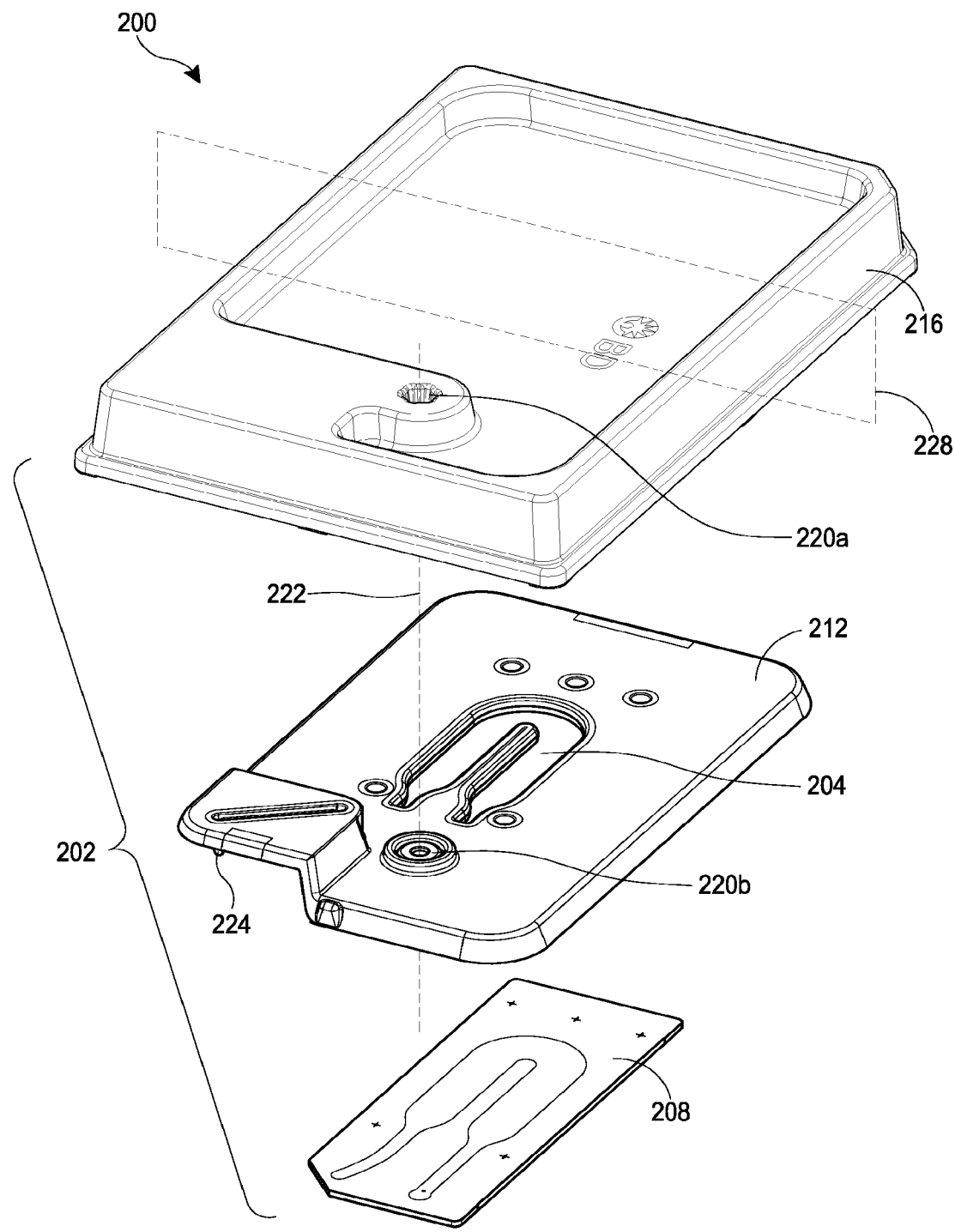
FIG. 2 is an exploded view of a cartridge that can be used with the loading station of FIG. 1.

FIG. 2 shows an exploded view of an embodiment of a cartridge 200 that can be used with the loading station 100. The cartridge 200 can include a flowcell 202 with a fluidic channel 204 formed by a microwell array substrate 208, a fluid channel layer 212, and a cover plate 216. The number of layers forming the flowcell 200 can be different in different implementations, ranging from 1 to 20. In some embodiments, the number of layers forming the flowcell 200 can be, or be about, 1, 2, 3, 4, 5, 6, 7, 8, 9, 10, 11, 12, 13, 14, 15, 16, 17, 18, 19, 20, or a number or a range between any two of these values. In some embodiments, the number of layers forming the flowcell 200 can be at least, or at most, 1, 2, 3, 4, 5, 6, 7, 8, 9, 10, 11, 12, 13, 14, 15, 16, 17, 18, 19, 20.

As shown in FIG. 2, the cartridge 200 can include an inlet port, formed by inlet port components 220a and 220b on the cover plate 216 and the fluidic channel layer 212 respectively. The inlet port components 220a and 220b can be coaxial along the axis 222. The cartridge 200 includes one outlet port 224 on the fluidic channel layer 212. The locations of the outlet port can be different in different implementations. In some embodiments, the outlet port can be on the cover plate 216. In some embodiments, the outlet port can be formed by outlet port components on the cover plate 216 and the fluidic channel layer 212.

The cartridge 200 or the flowcell 202 can include (i) one or more inlet ports for creating fluid connections with the instrument or manually introducing cell samples, bead suspensions, or other assay reagents into the cartridge. The flowcell can include one or more of (ii) one or more bypass channels, i.e. for self-metering of cell samples and bead suspensions, to avoid overfilling or back flow, (iii) one or more integrated microwell array/flowcell assemblies, or one or more chambers within which the microarray substrate(s) are positioned, (iv) integrated miniature pumps or other fluid actuation mechanisms for controlling fluid flow through the device, (v) integrated miniature valves (or other containment mechanisms) for compartmentalizing pre-loaded reagents (for example, bead suspensions) or controlling fluid flow through the device, (vi) one or more vents for providing an escape path for trapped gas, (vii) one or more sample and reagent waste reservoirs, (viii) one or more outlet ports for creating fluid connections with the instrument or providing a processed sample collection point. (ix) mechanical interface features for reproducibly positioning the removable, consumable cartridge with respect to the instrument system, and for providing access so that external magnets can be brought into close proximity with the microwell array, (x) integrated temperature control components or a thermal interface for providing good thermal contact with the instrument system, (xi) optical interface features, e.g. a transparent window, for use in optical interrogation of the microwell array, or any combination thereof.

Figure 3:
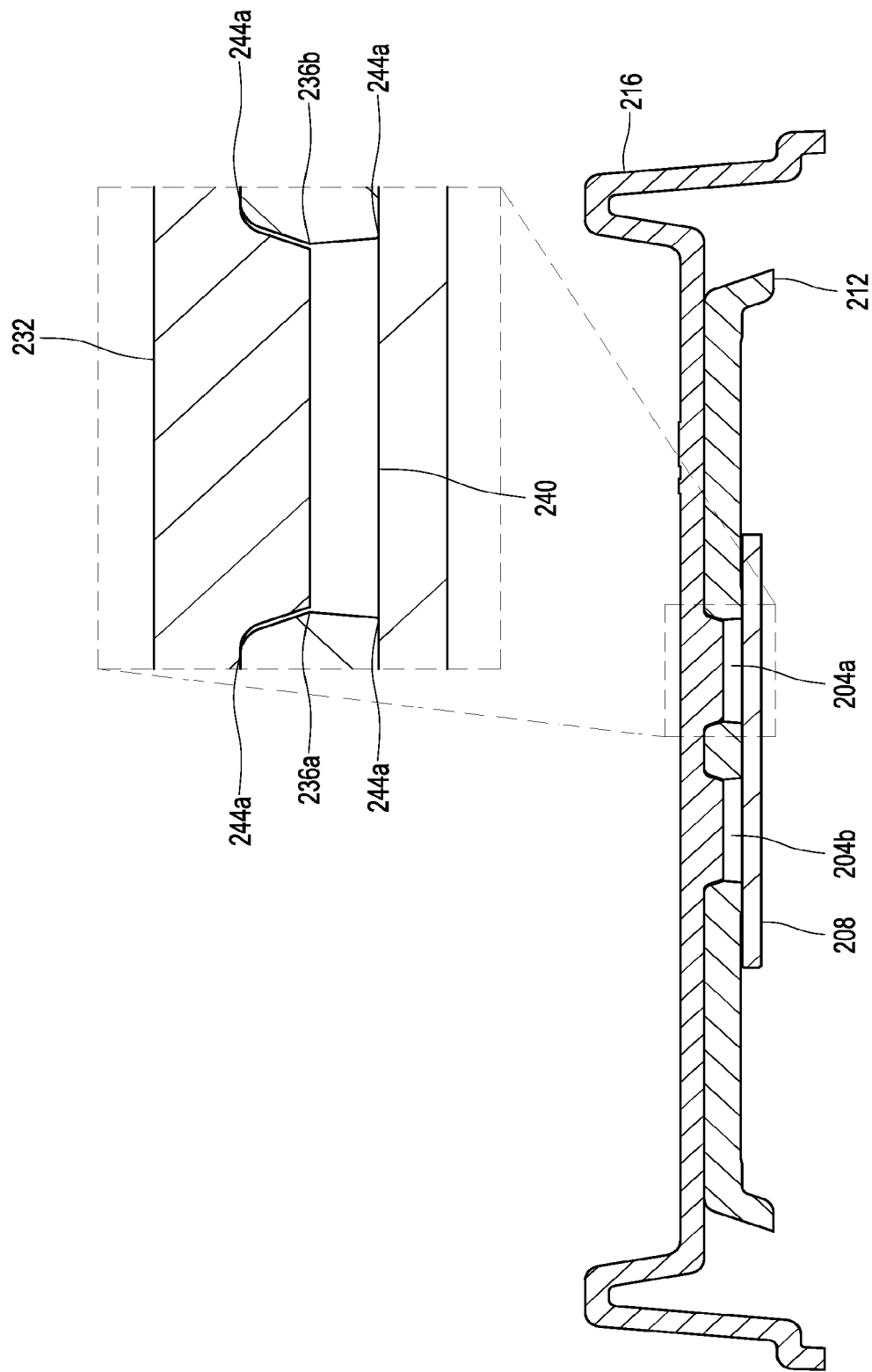
FIG. 3 is a cross-sectional view of the cartridge of FIG. 2.

FIG. 3 shows a cross-sectional view of the cartridge 200 taken along the plane 228 in FIG. 2. FIG. 3 shows two fluidic channel sections 204a and 204b of the fluidic channel 204. The fluidic channel section 204a comprises a fluidic channel ceiling 232, two fluidic channel sidewalls 236a and 236b (also referred to as a first sidewall 236a and a second sidewall 236b), and a fluidic channel bottom 240. The fluidic channel ceiling 232 and the fluidic channel sidewall 236a form an edge 244a (also referred to as a ceiling-first sidewall edge). The fluidic channel ceiling 232 and the fluidic channel sidewall 236b form another edge 244b (also referred to as a ceiling-second sidewall edge). The fluidic channel sidewalls 236a and 236b can have positive draft angles with respect to the fluidic channel ceiling 232, for example, ranging from 1-15 degrees. In some embodiments, the draft angle of the fluidic channel sidewall 236a or 236b with respect to the fluidic channel ceiling 232 can be, or be about, 1, 2, 3, 4, 5, 6, 7, 8, 9, 10, 11, 12, 13, 14, 15 degrees, or a number or a range between any two of these values. In some embodiments, the draft angle of the fluidic channel sidewall 236a or 236b with respect to the fluidic channel ceiling 232 can be at least, or at most, 1, 2, 3, 4, 5, 6, 7, 8, 9, 10, 11, 12, 13, 14, or 15 degrees.

The fluidic channel bottom 240 and the fluidic channel sidewall 236a form an edge 248a (also referred to as a bottom-first sidewall edge). The fluidic channel bottom 240 and the fluidic channel sidewall 236b form another edge 248b (also referred to as a bottom-second sidewall edge). The fluidic channel sidewalls 236a and 236b can have negative draft angles with respect to the fluidic channel bottom 240, for example, ranging from −1 to −15 degrees. In some embodiments, the draft angle of the fluidic channel sidewall 236a or 236b with respect to the fluidic channel bottom 240 can be, or be about, −1, −2, −3, −4, −5, −6, −7, −8, −9, −10, −11, −12, −13, −14, −15 degrees, or a number or a range between any two of these values. In some embodiments, the draft angle of the fluidic channel sidewall 236a or 236b with respect to the fluidic channel bottom 240 can be at least, or at most, −1, −2, −3, −4, −5, −6, −7, −8, −9, −10, −11, −12, −13, −14, or −15 degrees.

Figure 4:
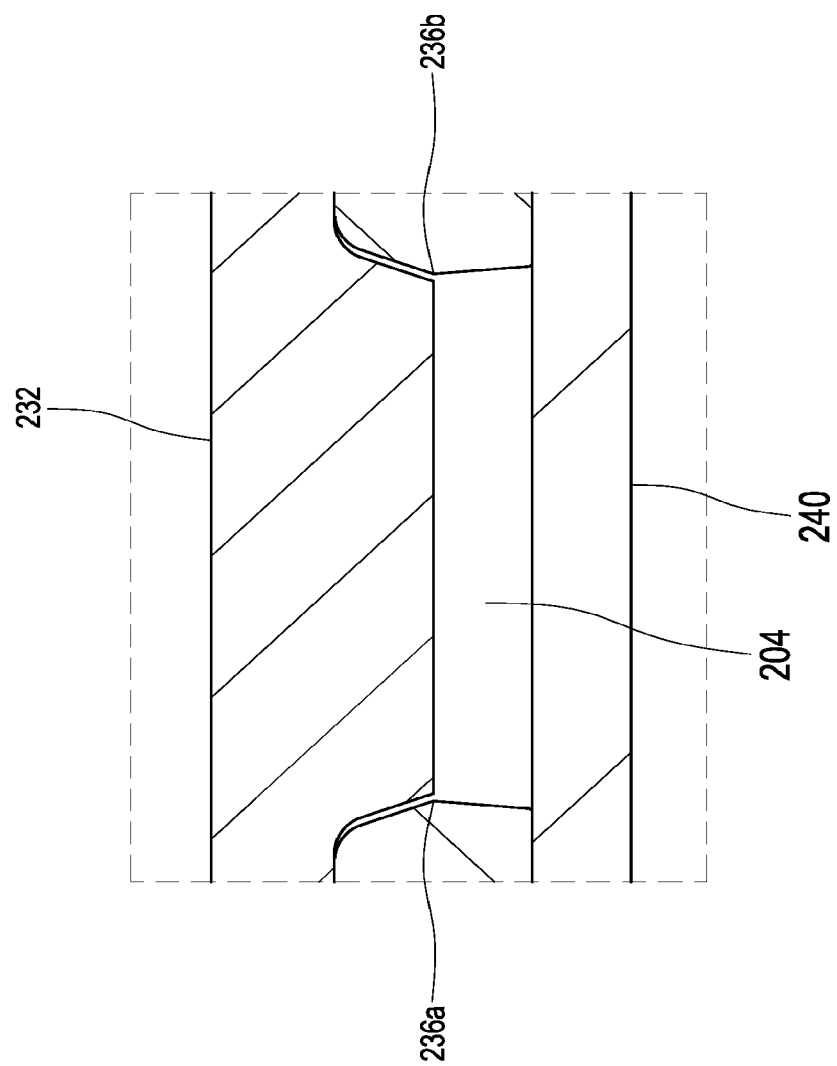
FIG. 4 is a cross-sectional view of a channel of the cartridge of FIG. 2.

FIG. 4 shows a cross-sectional view of an exemplary fluidic channel 204 of a cartridge 200. The fluidic channel 204 comprises a fluidic channel ceiling 232, two fluidic channel sidewalls 236a and 236b, and a fluidic channel bottom 240. The fluidic channel ceiling 232 and the fluidic channel sidewall 236a form an edge. The fluidic channel ceiling 232 and the fluidic channel sidewall 236b form another edge. The fluidic channel sidewalls 236a and 236b have positive draft angles, for example, ranging from 1-15 degrees. The width and the height of the fluidic channel 204 shown in FIG. 4 can be 7 mm and 1.2 mm respectively.

The width of the fluidic channel 204 can be different in different implementations, for example, ranging from 1 mm to 20 mm. In some embodiments, the width of the fluidic channel 204 can be, or be about, 1, 2, 3, 4, 5, 6, 7, 8, 9, 10, 11, 12, 13, 14, 15, 16, 17, 18, 19, 20 mm, or a number or a range between any two of these values. In some embodiments, the width of the fluidic channel 204 can be at least, or at most, 1, 2, 3, 4, 5, 6, 7, 8, 9, 10, 11, 12, 13, 14, 15, 16, 17, 18, 19, or 20 mm. A larger width, for example 7 mm, can increase the flowcell area of a given flowcell length.

The height of the fluidic channel 204 can be different in different implementations, for example, ranging from 0.1 mm to 2 mm. In some embodiments, the height of the fluidic channel 704 can be, or be about, 0.1, 0.2, 0.3, 0.4, 0.5, 0.6, 0.7, 0.8, 0.9, 0.10, 0.11, 0.12, 0.13, 0.14, 0.15, 0.16, 0.17, 0.18, 0.19, 0.20 mm, or a number or a range between any two of these values. In some embodiments, the height of the fluidic channel 204 can be at least, or at most, 0.1, 0.2, 0.3, 0.4, 0.5, 0.6, 0.7, 0.8, 0.9, 0.10, 0.11, 0.12, 0.13, 0.14, 0.15, 0.16, 0.17, 0.18, 0.19, or 0.20 mm.

The cartridge can be designed to process more than one sample in parallel. The cartridge can further comprise one or more removable sample collection chamber(s) that are suitable for interfacing with stand-alone PCR thermal cyclers or sequencing instruments. The cartridge itself can be suitable for interfacing with stand-alone PCR thermal cyclers or sequencing instruments. The term "cartridge" as used in this disclosure can be meant to include any assembly of parts which contains the sample and beads during performance of the assay.

The cartridge can further comprise components that are designed to create physical or chemical barriers that prevent diffusion of (or increase path lengths and diffusion times for) large molecules in order to minimize cross-contamination between microwells. Examples of such barriers can include, but are not limited to, a pattern of serpentine channels used for delivery of cells and solid supports (e.g., beads) to the microwell array, a retractable platen or deformable membrane that is pressed into contact with the surface of the microwell array substrate during lysis or incubation steps, the use of larger beads, e.g. Sephadex beads as described previously, to block the openings of the microwells, or the release of an immiscible, hydrophobic fluid from a reservoir within the cartridge during lysis or incubation steps, to effectively separate and compartmentalize each microwell in the array.

Cartridges can be fabricated using a variety of techniques and materials known to those of skill in the art. In general, the cartridges will be fabricated as a series of separate component parts and subsequently assembled using any of a number of mechanical assemblies or bonding techniques. Examples of suitable fabrication techniques include, but are not limited to, conventional machining, CNC machining, injection molding, thermoforming, and 3D printing. Once the cartridge components have been fabricated they can be mechanically assembled using screws, clips, and the like, or permanently bonded using any of a variety of techniques (depending on the choice of materials used), for example, through the use of thermal bonding/welding or any of a variety of adhesives or adhesive films, including epoxy-based, acrylic-based, silicone-based, UV curable, polyurethane-based, or cyanoacrylate-based adhesives.

Cartridge components can be fabricated using any of a number of suitable materials, including but not limited to silicon, fused-silica, glass, any of a variety of polymers, e.g. polydimethylsiloxane (PDMS; elastomer), polymethylmethacrylate (PMMA), polycarbonate (PC), polypropylene (PP), polyethylene (PE), high density polyethylene (HDPE), polyimide, cyclic olefin polymers (COP), cyclic olefin copolymers (COC), polyethylene terephthalate (PET), epoxy resins, non-stick materials such as teflon (PTFE), metals (e.g. aluminum, stainless steel, copper, nickel, chromium, and titanium), or any combination thereof.

The inlet and outlet features of the cartridge can be designed to provide convenient and leak-proof fluid connections with the instrument, or can serve as open reservoirs for manual pipetting of samples and reagents into or out of the cartridge. Examples of convenient mechanical designs for the inlet and outlet port connectors can include, but are not limited to, threaded connectors, Luer lock connectors, Luer slip or "slip tip" connectors, press fit connectors, and the like. The inlet and outlet ports of the cartridge can further comprise caps, spring-loaded covers or closures, or polymer membranes that can be opened or punctured when the cartridge is positioned in the instrument, and which serve to prevent contamination of internal cartridge surfaces during storage or which prevent fluids from spilling when the cartridge is removed from the instrument. The one or more outlet ports of the cartridge can further comprise a removable sample collection chamber that is suitable for interfacing with stand-alone PCR thermal cyclers or sequencing instruments.

In some embodiments, the inlet port and the outlet port can be capable of directing a flow of a fluid through the fluidic channel, thereby contacting the microwells with the fluid. In some embodiments, the device comprises a pipette tip interface for loading or removing a cell sample, an assay reagent, a bead suspension, waste from the device, or a combination thereof. The device can comprise the cell sample, the assay reagent, the bead suspension, or a combination thereof.

The cartridge can include integrated miniature pumps or other fluid actuation mechanisms for control of fluid flow through the device. Examples of suitable miniature pumps or fluid actuation mechanisms can include, but are not limited to, electromechanically- or pneumatically-actuated miniature syringe or plunger mechanisms, membrane diaphragm pumps actuated pneumatically or by an external piston, pneumatically-actuated reagent pouches or bladders, or electro-osmotic pumps.

The cartridge can include miniature valves for compartmentalizing pre-loaded reagents or controlling fluid flow through the device. Examples of suitable miniature valves can include, but are not limited to, one-shot "valves" fabricated using wax or polymer plugs that can be melted or dissolved, or polymer membranes that can be punctured; pinch valves constructed using a deformable membrane and pneumatic, magnetic, electromagnetic, or electromechanical (solenoid) actuation, one-way valves constructed using deformable membrane flaps, and miniature gate valves.

The cartridge can include vents for providing an escape path for trapped air or gas such as $CO_2$ or $N_2$. Vents can be constructed according to a variety of techniques, for example, using a porous plug of polydimethylsiloxane (PDMS) or other hydrophobic material that allows for capillary wicking of air or gas but blocks penetration by water.

The mechanical interface features of the cartridge can provide for easily removable but highly precise and repeatable positioning of the cartridge relative to the instrument system. Suitable mechanical interface features can include, but are not limited to, alignment pins, alignment guides, mechanical stops, and the like. The mechanical design features can include relief features for bringing external apparatus, e.g. magnets or optical components, into close proximity with the microwell array chamber.

The cartridge can include temperature control components or thermal interface features for mating to external temperature control modules. Examples of suitable temperature control elements can include, but are not limited to, resistive heating elements, miniature infrared-emitting light sources, Peltier heating or cooling devices, heat sinks, thermistors, thermocouples, and the like. Thermal interface features can be fabricated from materials that are good thermal conductors (e.g. copper, gold, silver, etc.) and can comprise one or more flat surfaces capable of making good thermal contact with external heating blocks or cooling blocks.

The cartridge can include optical interface features for use in optical imaging or spectroscopic interrogation of the microwell array. The cartridge can include an optically transparent window, e.g. the microwell substrate itself or the side of the flowcell or microarray chamber that is opposite the microwell array, fabricated from a material that meets the spectral requirements for the imaging or spectroscopic technique used to probe the microwell array. Examples of suitable optical window materials can include, but are not limited to, glass, fused-silica, polymethylmethacrylate (PMMA), polycarbonate (PC), cyclic olefin polymers (COP), or cyclic olefin copolymers (COC).

Loading Station and Cartridge

Figure 5:
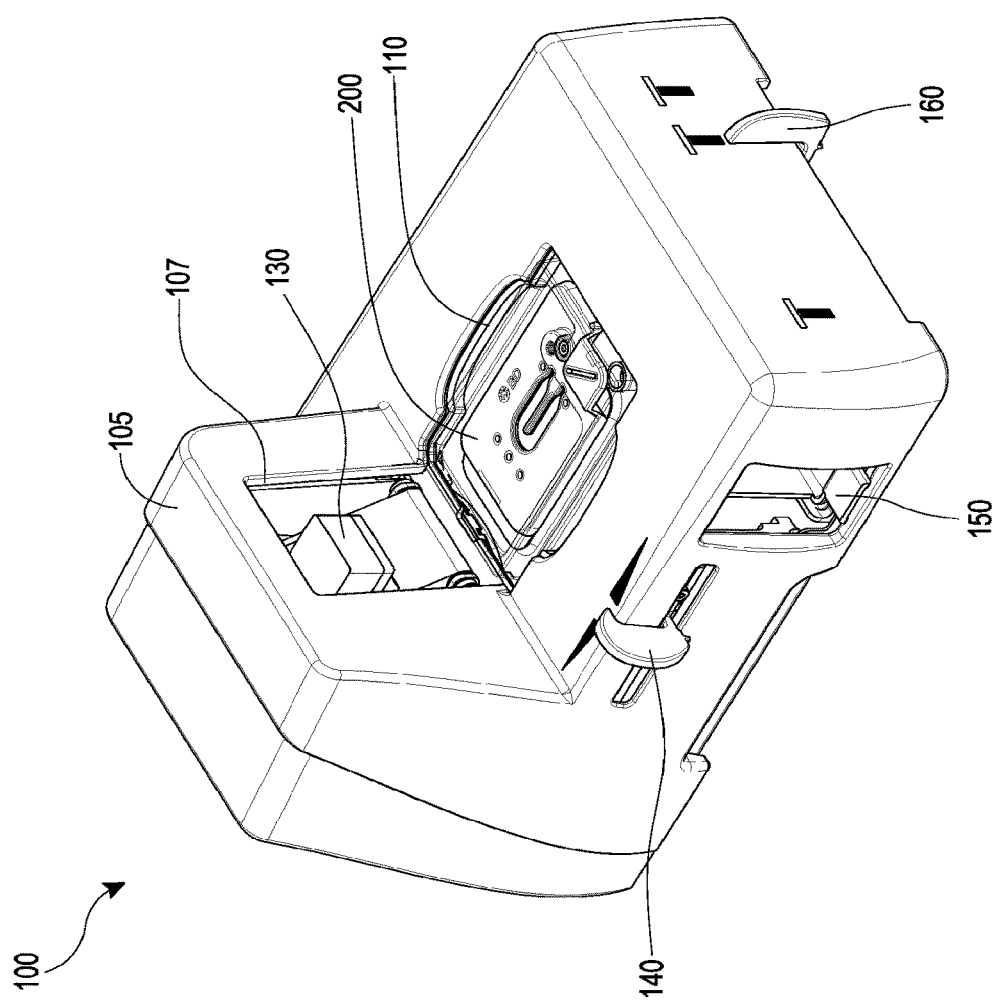
FIG. 5 is a perspective view of the loading station of FIG. 1 in engagement with the cartridge of FIG. 2.

FIG. 5 shows the loading station 100 with the cartridge 200 positioned within the tray 110. As described herein, the loading station 100 can facilitate performance of a workflow using the microwell array of the microwell array substrate 208. For example, in some embodiments, one or both of the inlet port components formed by inlet port components 220a and 220b can be configured to receive a pipette for introduction of one or more particles or other materials. In some embodiments, the tray 110 can secure the cartridge 200 within the loading station during pipetting. In some embodiments, the tray 110 can secure the cartridge 200 within the loading station during introduction and/or removal of the pipette.

As shown in FIG. 5, the actuator 140 of the loading station 100 is in its first or neutral position. As described herein, when the actuator 140 is in the neutral position, both the magnet 120 and the magnet 130 exert relatively weak or no force on any magnetic particles positioned in the flowcell 202 and/or microwell array of the cartridge 200. When relatively weak or no magnetic force is exerted on particles positioned in the flowcell 202 and/or microwell array, the particles may be washed by fluids introduced into the flowcell 202 of the cartridge 200, for example, through the inlet port components 220a and 220b. In some embodiments, fluid introduced into the flowcell 202 of the cartridge 200 can wash particles within the flowcell 202 and/or microwell array by transporting the particles out of the flowcell 202 through the outlet port 224.

As shown in FIG. 5, the actuator 160 is positioned in the second position. As described herein, when the actuator 160 is positioned in the second position, the drawer 150 can also be positioned in its second position. In some embodiments, the second position of the drawer 150 can be designated as a waste collection position. In such embodiments, the one of the tubes 152a or 152b that is aligned with the outlet port 224 can be designated as a waste collection tube.

A user can position the actuator 160 in its second position when collection of waste is desirable to allow fluid and particles flowing through the flowcell 202 of the cartridge 200 to flow out of the outlet port 224 and into the one of the tubes 152a and 152b aligned with the outlet port 224.

As described herein, the actuator 160 can be transitioned to the third position, which can cause the drawer 150 to transition to its third position. When the drawer 150 is in its third position, the other one of the tubes 152a and 152b can align with the outlet port 224. In some embodiments, the third position of the drawer 150 can be designated as the bead collection position. The other one of the tubes 152a and 152b can be designated as the bead collection tube.

A user can position the actuator 160 in its second position when collection of beads is desirable to allow beads within the flowcell 202 and/or micro well array of the cartridge 200 to flow out of the outlet port 224 and into the one of the tubes 152a and 152b aligned with the outlet port 224.

Figure 6:
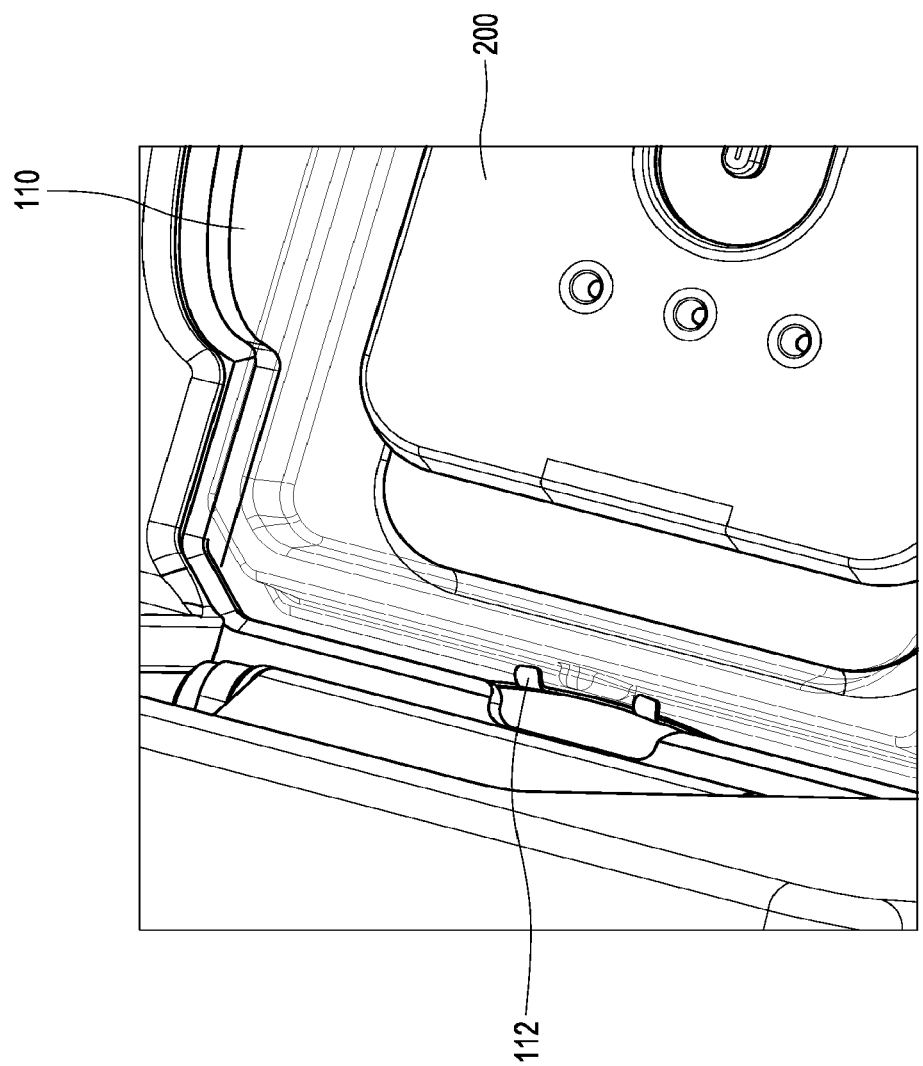
FIG. 6 is an enlarged view of a section of the loading station and cartridge of FIG. 5.

FIG. 6 shows an enlarged view of the portion of the loading station 100 with the cartridge 200 positioned within the tray 110. As shown in FIG. 6, the loading station 100 can include a locking member 112. The locking member 112 can secure the cartridge 200 within the tray 110. In some embodiments, the locking member 112 is a spring clip. In some embodiments, the cartridge 200 can be secured to the tray 110 by inserting the cartridge 200 so that a portion of the cartridge 200 is positioned between the locking member 112 and the tray 110. In some embodiments, the locking member 112 is retractable within the body 105 of the loading station 100. In some embodiments, the cartridge 200 can be secured to the tray 110 by positioning the cartridge 200 within the tray 110 and advancing the locking member 112 so that locking member 112 is positioned superior to a superior surface of the cartridge 200 such that the cartridge 200 is positioned between the locking member 112 and the tray 110.

Figure 7:
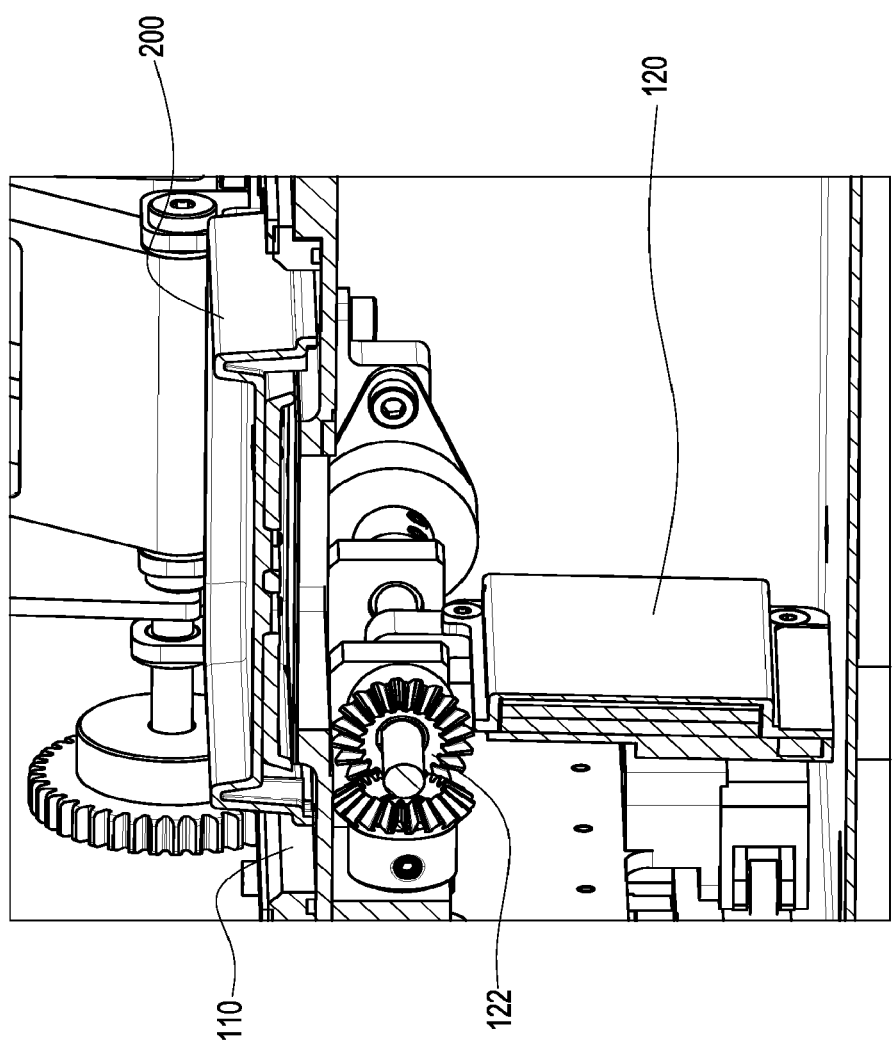
FIG. 7 is an enlarged view of a section of the loading station and cartridge of FIG. 5 showing internal features.

FIG. 7 shows an enlarged sectional view of the loading station 100 and cartridge 200 with several components removed to show internal features of the loading station 100. FIG. 7 depicts the magnet 120 in its inactive position. As described herein, the inactive position of the magnet 120 corresponds to first position of the actuator 140 as shown in FIG. 5. FIG. 7 shows a plurality of gears forming a gear mechanism 122 in communication with the magnet 120. Movement of the actuator 140 between its first and second position can activate the gear mechanism 122 to cause movement of the magnet 120 between its inactive and active position.

Figure 8:
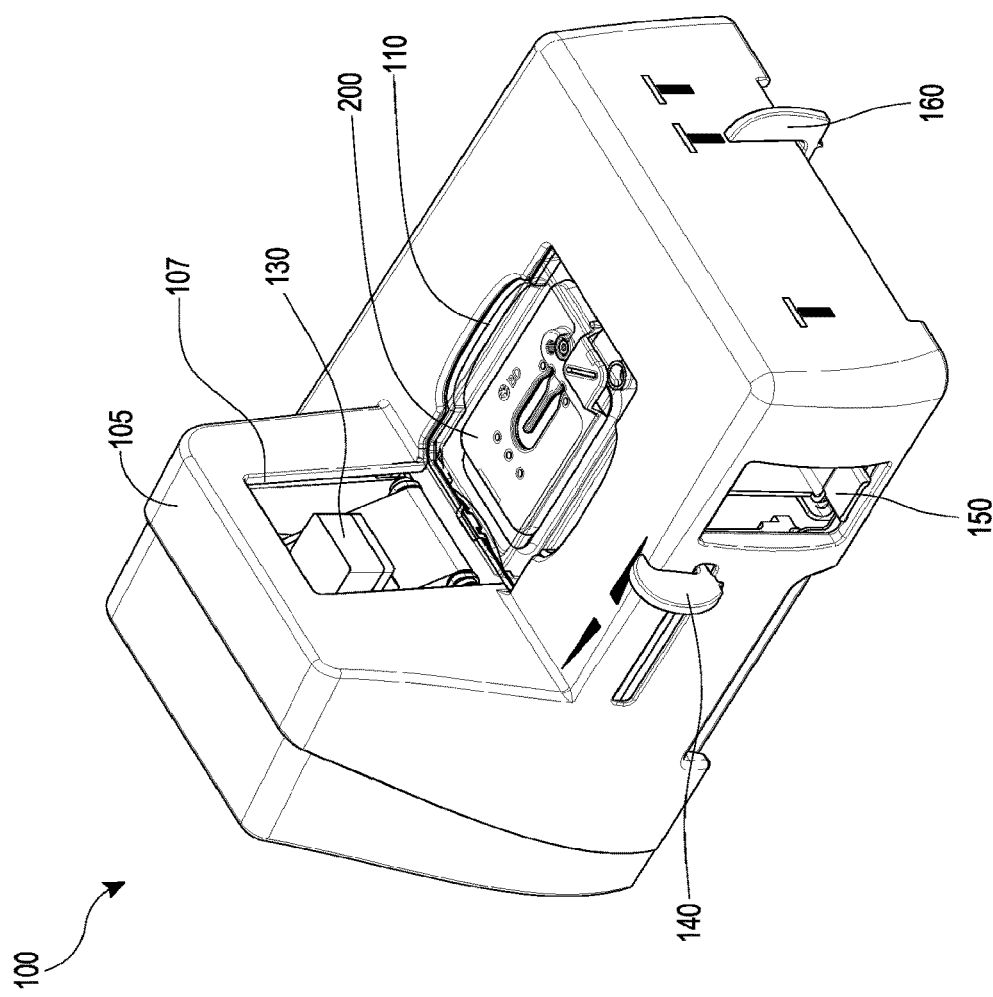
FIG. 8 is a perspective view of the loading station and cartridge of FIG. 5.

FIG. 8 shows the loading station 100 and cartridge 200 with the actuator 140 in its second position. As described herein, transition of the actuator 140 from the first position to the second position can cause the magnet 120 to transition from its inactive position to its active position.

Figure 9:
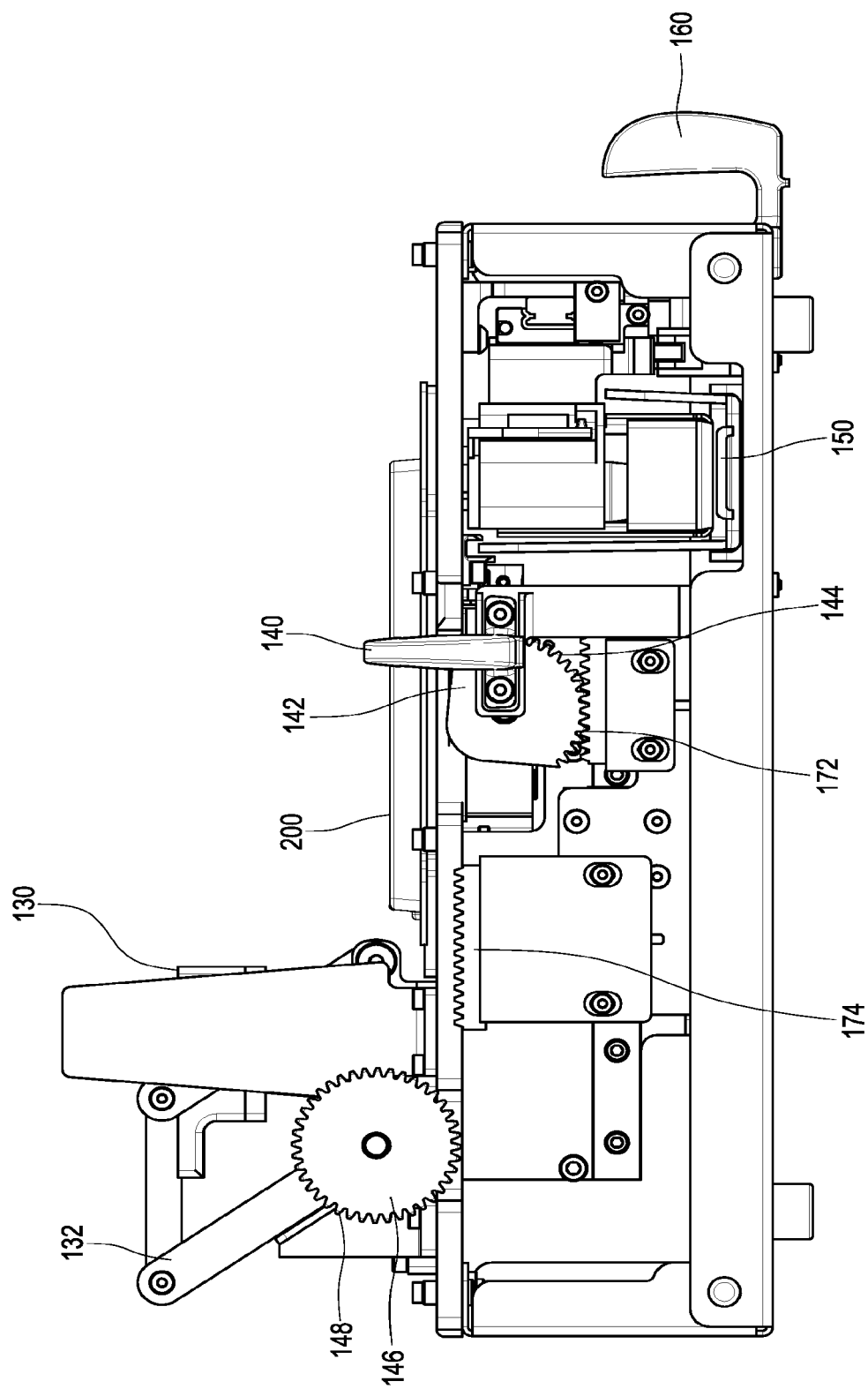
FIG. 9 is a side view of the loading station and cartridge of FIG. 5 showing internal features.

FIG. 9 shows a side view of the loading station 100 and cartridge 200 with several components removed to show internal features. As shown in FIG. 9, the actuator 140 is in the second position. When transitioned to the second position, the actuator 140 can engage a gear 142. The gear 142 includes a plurality of teeth 144 extending at least partially around an edge of the gear 142. In some embodiments, the loading station 100 can include a set of teeth 172 positioned to engage the teeth 144 when the actuator 140 is transitioned from the first position to the second position. In some embodiments, as the actuator 140 is transitioned from its first position to its second position, the actuator 140 causes the teeth 144 to advance along the teeth 172 to cause rotation of the gear 142. In some embodiments, the gear 142 is coupled to a shaft that is coupled to the gear mechanism 122 such that rotation of the gear 142 causes activation of the gear mechanism 122. As described herein, activation of the gear mechanism 122 can cause movement of the magnet 120. In some embodiments, as the actuator 140 transitions from the first position to the second position, the gear mechanism 122 causes the magnet 120 to transition from the inactive position to the active position. If the actuator 140 transitions from the second position to the first position, the actuator 140 can cause the gear 142 to advance along the teeth 172 so as to cause rotation of the gear 142 in an opposite direction of that when the actuator 140 is transitioned from the first position to the second position. In some embodiments, as the actuator 140 transitions from the second position to the first position, the gear mechanism 122 causes the magnet 120 to transition from the active position to the inactive position.

With continued reference to FIG. 9, the loading station 100 can also include a set of teeth 174. In some embodiments, the actuator 140 can be configured to engage the set of teeth 174 when the actuator transitions from the first position to the third position. In some embodiments, the actuator 140 can be configured to cause the set of teeth 174 to translate within the body 104 of the loading station 100 when the actuator 140 transitions from the first position to the third position. In some embodiments, the loading station 100 can include a gear 146 having a plurality of teeth 148. In some embodiments, when the actuator 140 transitions between the first position to the third position, the teeth 174 can engage the teeth 148 of the gear 146 to cause the gear 146 to rotate. The gear 146 can be coupled to a shaft that is also coupled to a link assembly 132. The link assembly 132 can include a plurality of links coupled to the magnet 130. Rotation of the gear 146 can cause movement of the link assembly 132 to cause the magnet 130 to transition between the inactive position and the active position. In some embodiments, transition of the actuator 140 from the first position to the third position causes rotation of the gear 146 such that the link assembly 132 moves to cause the magnet 130 to transition from its inactive position to its active position. In some embodiments, transition of the actuator 140 from the third position to the first position causes rotation of the gear 146 such that the link assembly 132 moves to cause the magnet 130 to transition from the active position to the inactive position. The actuator 140, gear 142, gear 146, set of teeth 172, and set of teeth 174 can each be members of an actuation mechanism. In some embodiments, the actuator can only actuate 140 one of the gear 142 and gear 146 at a time. As shown in FIG. 9, in some embodiments, the actuator can only actuate one of the gear 142 and gear 146 due to the relative positioning of the gear 142 and the gear 146. In some embodiments, the actuation mechanism can be configured to couple to only one of the gear 142 and gear 146 in any position of the actuator 140. In some embodiments, the actuation mechanism can be configured to cause movement of only one of the magnet 120 and magnet 130 in any position.

Figure 10:
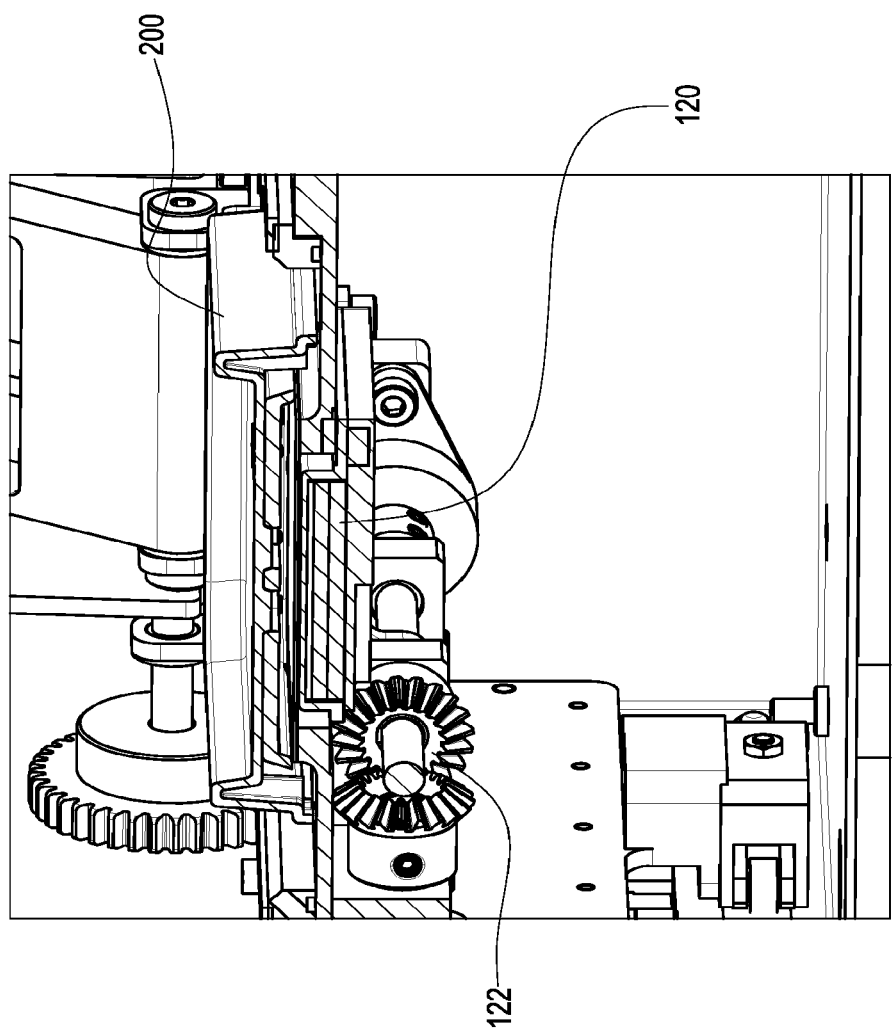
FIG. 10 is an enlarged view of a section of the loading station and cartridge of FIG. 5 showing internal features.

FIG. 10 shows an enlarged sectional view of the loading station 100 and cartridge 200 with several components removed to show internal features of the loading station 100. FIG. 10 depicts the magnet 120 in its first position. In some embodiments, when the magnet 120 is in the second position, a superior face of the magnet 120 is in parallel with an inferior face of the cartridge 200. In some embodiments, the superior surface of the magnet 120 can be 1.0 mm away or approximately 1.0 mm away from the inferior surface of the cartridge 200 when in the active position. In some embodiments, the superior surface of the magnet 120 can be 0.5 mm, 1.5 mm, 2.0 mm, 2.5 mm, 3.0 mm, less than 0.5 mm, less than 1.0 mm, no more than 1.0 mm, less than 1.5 mm, less than 2.0 mm, less than 2.5 mm, less than 3.0 mm, or between 0.5 mm and 1.5 mm away from the inferior surface of the cartridge 200 when the magnet 120 is in the active position. In some embodiments, the superior surface of the magnet 120 can be sized and shaped to extend to or beyond the boundaries of an active area of the flowcell 202.

Figure 11:
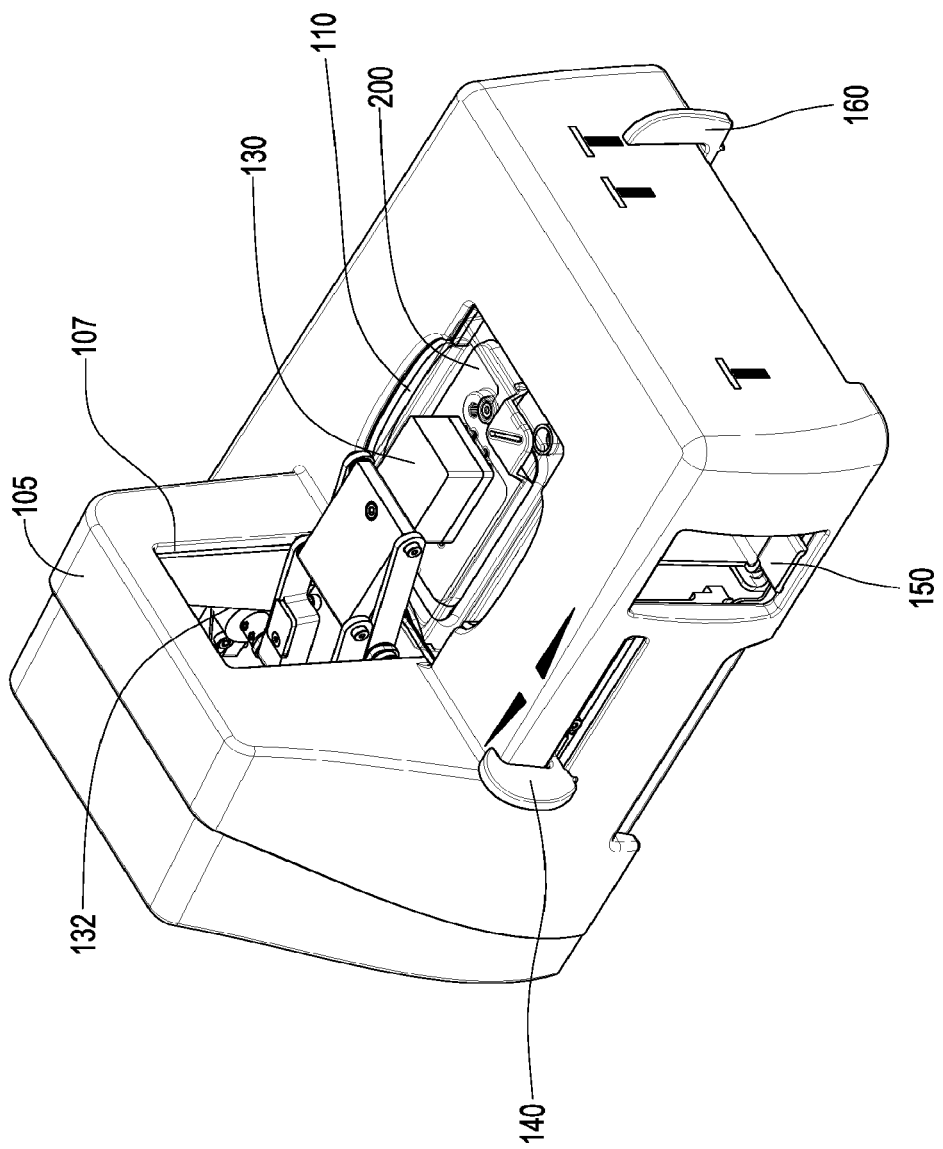
FIG. 11 is a perspective view of the loading station and cartridge of FIG. 5.

FIG. 11 shows the loading station 100 and cartridge 200 with the actuator 140 in its third position. As described herein, transition of the actuator 140 from the first position to the third position can cause the magnet 130 to transition from the inactive position to the active position. FIG. 11 shows the magnet 130 in the active position. In some embodiments, when the magnet 130 is in the active position, an inferior face of the magnet 130 can be positioned above a superior face of the cartridge 200. In some embodiments, the inferior face of the magnet 130 can be in parallel with the superior face of the cartridge 200. In some embodiments, the inferior surface of the magnet 130 can be 1.0 mm away or approximately 1.0 mm away from the superior surface of the cartridge 200 when in the active position. In some embodiments, the inferior surface of the magnet 130 can be 0.5 mm, 1.5 mm, 2.0 mm, 2.5 mm, 3.0 mm, less than 0.5 mm, less than 1.0 mm, no more than 1.0 mm, less than 1.5 mm, less than 2.0 mm, less than 2.5 mm, less than 3.0 mm, or between 0.5 mm and 1.5 mm away from the superior surface of the cartridge 200 when the magnet 130 is in the active position. In some embodiments, the inferior surface of the magnet 130 can be sized and shaped to extend to or beyond the boundaries of the active area of the flowcell 202.

Figure 12A:
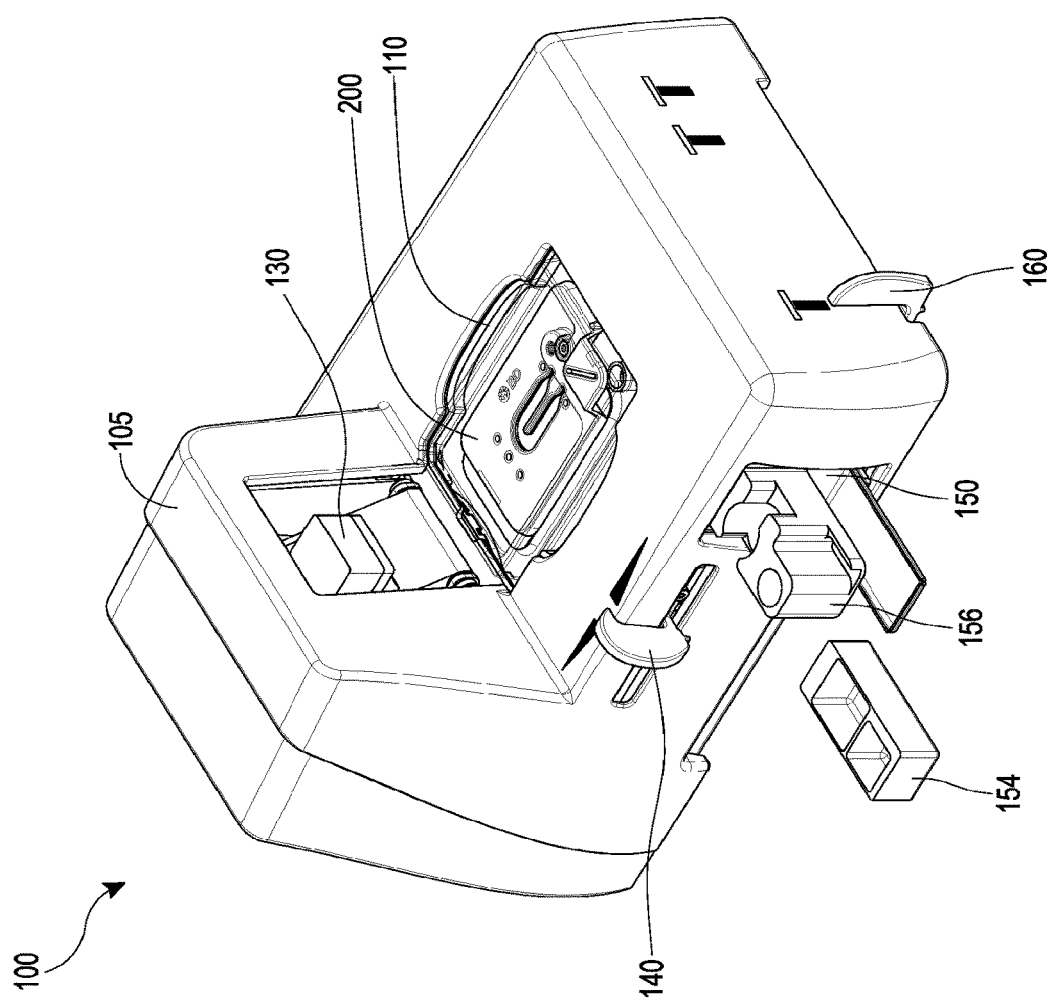
FIG. 12A is a partially exploded perspective view of the loading station and cartridge of FIG. 5.
Figure 12B:
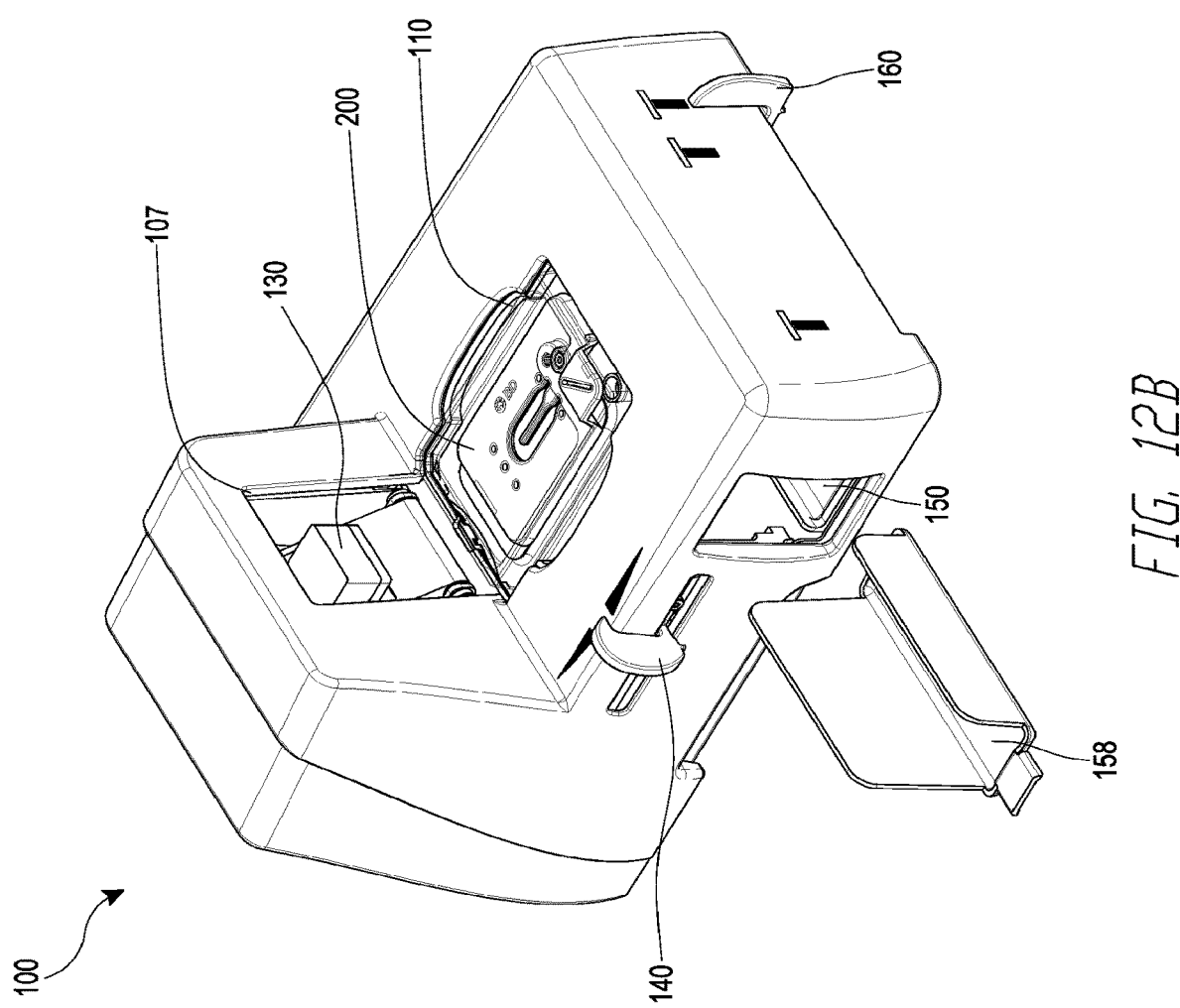
FIG. 12B is a partially exploded perspective view of the loading station and cartridge of FIG. 5.
Figure 13:
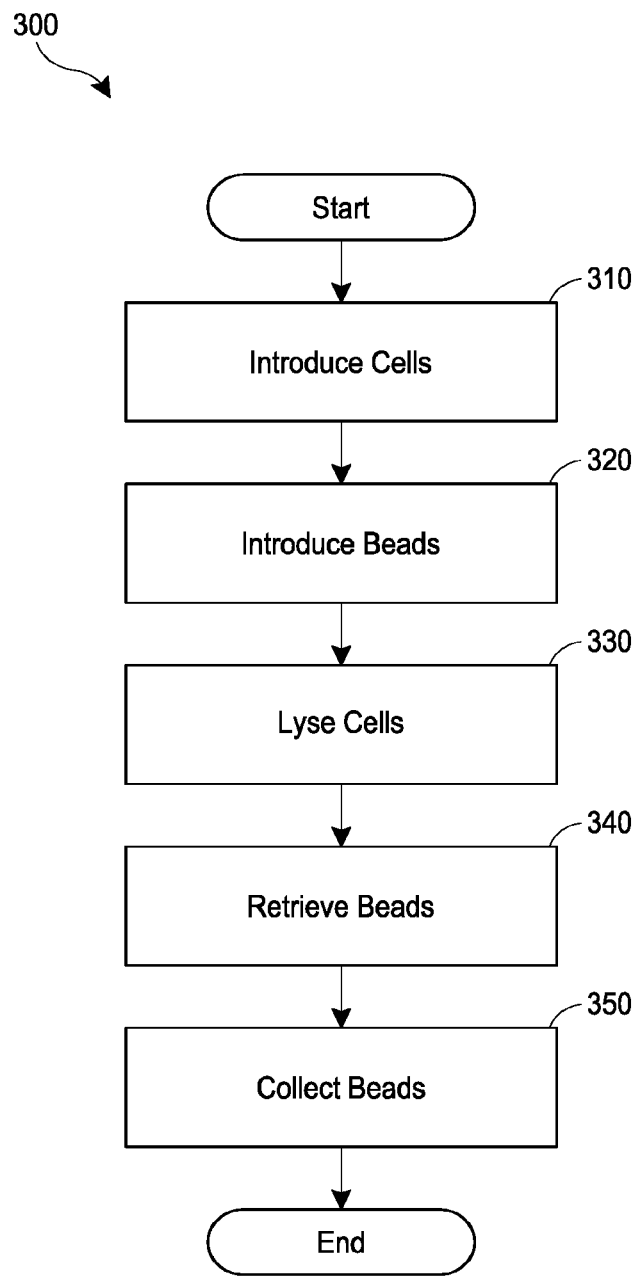
FIG. 13 is a flowchart depicting an example of a workflow that can be performed using the loading station and cartridge of FIG. 5.

FIGS. 12A and 12B shows the loading station 100 and cartridge 200 showing several components of the drawer 150 removed from the loading station 100. As shown in FIG. 12A, the drawer 150 can include a drip tray 154. The drip tray 154 can be positioned inferior to the tube receptacle 156. The drip tray 154 can be configured to receive liquid dripping or leaking from one or both of the tubes 152a and 152b. As shown in FIG. 12A, the drip tray 154 can be removable.

As shown in FIG. 12B, the drawer 150 can include a splash shield 158. In use, the splash shield 158 can be positioned within the interior of the body 105 and can at least partially surround a path of movement of the drawer 150. The splash shield 158 can form a barrier between the tubes 152a and 152b and other components of the loading station 100 to prevent splashing of liquid from the tubes 152a and 152 onto other components of the loading station 100.

Examples of Workflows

FIG. 12 depicts a non-limiting example of a workflow 300 that can be performed using a loading station 100 and cartridge 200. Although the workflow 300 is described with respect to the loading station 100 and cartridge 200, one of skill in the art would understand that the same workflow or a similar workflow may be performed using other embodiments of loading stations and cartridges as described herein.

The workflow 300 describes steps performed after the cartridge 200 is positioned within the tray 110 and the tubes 152a and 152b are positioned within the drawer 150. One of skill in the art would recognize that additional steps of inserting the cartridge 200 into the tray 110 and/or inserting the tubes 152a and 152b into the receptacle 156 of the drawer 150 may be required prior to initiation of the workflow 300 if the cartridge 200 and/or tubes 152a and 152b are not already in their respective positions within the loading station 100.

Additionally, the workflow 300 describes steps performed with the actuator 140 in its first position (corresponding to each of the magnets 120 and 130 being in their inactive positions) and the actuator 160 in its second position (corresponding to one of the tubes 152a and 152b being in a waste collection position) at the beginning of the workflow 300. One of skill in the art would recognize that additional steps may be required to move the actuator 140 and/or actuator 160 to their first and second positions, respectively, prior to initiation of the workflow.

The workflow 300 can begin with a step 310 in which a plurality of cells is introduced into a microwell array of the cartridge 200 while the cartridge 200 is positioned within the loading station 300. In some embodiments, the plurality of cells can be introduced into the cartridge 200 via the inlet formed by inlet port components 220a and 220b. In some embodiments, the plurality of cells can be introduced into the cartridge 200 via a pipette. In some embodiments, the plurality of cells can enter the microwell array via the flowcell 202 of the cartridge 200. In some embodiments, each microwell in the microwell array can entrap only a single cell of the plurality of cells.

In alternative embodiments, the plurality of cells can be introduced into the microwell array prior to positioning of the cartridge 200 within the loading station 100.

After the plurality of cells are introduced into the microwell array, a plurality of barcode-bearing beads can be introduced into the microwell array at a step 320. In some embodiments, the plurality of beads can be introduced into the cartridge 200 via the inlet formed by inlet port components 220a and 220b. In some embodiments, the plurality of beads can be introduced into the cartridge 200 via a pipette. In some embodiments, the plurality of beads can enter the microwell array via the flowcell 202 of the cartridge 200. In alternative embodiments, the plurality of beads can be introduced into the microwell array prior to positioning of the cartridge 200 within the loading station 100. It would be appreciated by one of skill in the art that the order in which the cells are introduced (block 310) and the beads are introduced (block 320) occur is not particularly limited. The two steps can occur concurrently or sequentially, and any order is within the scope of the present disclosure.

In some embodiments, each microwell in the microwell array can entrap only a single bead of the plurality of beads. In some embodiments, each microwell in the microwell array can entrap a single cell of the plurality of cells and a single bead of the plurality of beads.

After the plurality of beads are introduced into the microwell array, cell lysis can be performed at a step 330. In some embodiments, the cell lysis can be performed before the plurality of beads are introduced into the microwell array.

Cell lysis can be accomplished by any of the variety of means described herein. In some embodiments, step 330 includes transitioning the magnet 120 to its active position prior to or during cell lysis, as shown and described with respect to FIG. 10. As described herein, the magnet 130 can be transitioned to its active position by moving the actuator 140 to its second position.

When the magnet 120 is in the active position, the magnet 120 can attract the barcoded-bearing beads positioned within the microwells. Due to the positioning of the magnet 120, the magnetic field generated by the magnet 120 can provide a magnetic force drawing the beads in the inferior direction towards the magnet 120. In some embodiments, the magnetic force generated by the magnet 120 can maintain the beads in the microwells during lysis. In some embodiments, the beads can be dimensioned such that a bead positioned superior to a cell within a microwell can prevent passage of the cell out of the microwell without removal of the bead from the microwell. In such embodiments, the magnetic force generated by the magnet 120 can maintain the cells in the microwells during lysis by maintaining the beads in the microwells to prevent passage of the cells.

In some embodiments, lysis is performed by introducing a lysis buffer. In such embodiments, the magnet 120 can prevent beads and/or cells positioned within the microwells from being washed away by the lysis buffer. In some embodiments, during cell lysis, the one of the tubes 152a and 152b designated for waste collection can be aligned with the outlet of the flowcell 202 to receive excess buffer flowing through the flowcell 202. In some embodiments, the introduction of cells and beads results in cells and/or beads positioned within the flowcell 202 but outside of a microwell. In such embodiments, the cells and/or beads positioned outside of the microwells may be washed away by the lysis buffer into the one of the tubes 152a and 152b designated for waste collection.

In some embodiments, after lysis, the magnet 120 is returned to its inactive position. As described herein, the magnet can transition to the inactive position by movement of the actuator 140 from the second position to the first position.

In certain embodiments, a wash can be performed before, during, or after cell lysis. In some embodiments, a wash fluid can be introduced into the flowcell 202 of the cartridge 200 via the inlet port provided by inlet port components 220a and 220b. The wash fluid can flow through the flowcell 202 to remove beads and/or cells within the flowcell 202 but outside of a microwell. The removed beads and/or cells can be deposited in the one of the tubes 152a and 152b designated for waste collection and aligned with the outlet of the flowcell 202. During the wash, the magnet 120 can be maintained in the active position. The magnetic force provided by the magnet 120 can prevent the beads and/or cells positioned within the microwells from removal by the wash fluid. In embodiments in which a wash is performed after cell lysis, the magnet 120 can be returned to its inactive position following the wash.

After cell lysis, the barcode-bearing beads can be retrieved at step 340. In some embodiments, the barcode-bearing beads are retrieved by advancing the magnet 130 from its inactive position to its active position. As described herein, the magnet 130 can be advanced from its inactive position to its active position by movement of the actuator 140 between the first position and the third position.

When the magnet 130 is positioned in the active position, the magnet 130 can attract the barcode-bearing beads positioned within the microwells. In some embodiments, the magnetic force exerted on the barcode-bearing beads by the magnet 130 can be sufficient to remove the barcode bearing beads from the microwells. When the barcode-bearing beads are removed by the magnet 130, the cells may remain within the microwells. In some embodiments, the magnetic force exerted on the barcode-bearing beads by the magnet 130 can cause the barcode bearing beads to move towards the superior surface of the cartridge 200. The magnetic force exerted by the magnet 130 can maintain the beads in a position superior to the microwells. While the beads are maintained in a position superior to the microwells, the beads can be said to be retrieved by the magnet 130.

While the beads are maintained in a position superior to the microwells by the magnet 130, a wash can be performed. In some embodiments, a wash fluid can be introduced into the flowcell 202 of the cartridge 200 via the inlet port provided by inlet port. The wash fluid can flow through the flowcell 202 to remove the cells in the microwells. The cells can be deposited in the one of the tubes 152a and 152b designated for waste collection and aligned with the outlet of the flowcell 202. Washing the cells from the microwells can allow for later collection of only the beads previously positioned in the microwells.

After the beads are retrieved by the magnet 130, the beads can be collected at step 350. In some embodiments, the magnet 130 is transitioned from its active position to its inactive position, releasing the beads from their maintained position superior to the microwells. As described herein the magnet 130 can be transitioned from its active position to its inactive position by movement of the actuator 140 from its third position to its first position. In some embodiments, upon release, the beads drop or return into the same microwells from which they were removed.

After the beads are released, the one of the tubes 152a and 152b designated for bead collection can be aligned with the outlet port 224 of the cartridge 200. As described herein, the tube 152a or 152b designated for bead collection can be aligned with the outlet port 224 by transitioning the actuator 160 from its second position to its third position. After the tube 152a or 152b designated for bead collection is aligned with the outlet port 224a, a fluid can be advanced through the flowcell 202 to cause the beads to flow out of the outlet port 224 and into the collection tube 152a or 152b designated for bead collection. To allow collection of the beads, it can be desirable that each of the magnets 120 and 130 are positioned in their respective inactive positions during collection. In other words, it can be desirable that neither magnet 120 nor magnet 130 is exerting a magnetic force on the beads during collection.

After the beads are collected, the workflow 300 concludes. In some embodiments, after collection of the beads, the tube 152a or 152b designated for bead collection can be removed from the loading station 100 for further processing and/or analysis of the beads.

The workflow 300 describes one example of a workflow that can be performed using the loading station 100 and cartridge 200. However, the loading station 100 can be used to perform different workflows. In some embodiments, the loading station 100 can be used to perform workflows on different cartridges.

One of skill in the art would also recognize that various alternative embodiments of the loading station 100 can be used to perform the steps of the workflow 300 or other procedures described herein. In some embodiments, the loading station 100 may include only a single magnet configured to move over a range of positions. For example, in some embodiments, the single magnet can be movable to the active position of the magnet 120 during performance of a lysis step, such as step 330. In some embodiments, the single magnet can be movable to the active position of magnet 130 during a retrieval step such as step 340. In certain embodiments, the single magnet can be moved to one or more other positions in which the single magnet does not exert a force or exerts a relatively weak force on the beads, for example, during a bead introduction step, such as step 320, or during a bead collection step, such as step 350. In some embodiments, the loading station 100 can have more than two magnets. In some embodiments, each magnet can have a separate actuator for transitioning between its inactive position and active position.

In at least some of the previously described embodiments, one or more elements used in an embodiment can interchangeably be used in another embodiment unless such a replacement is not technically feasible. It will be appreciated by those skilled in the art that various other omissions, additions and modifications may be made to the methods and structures described above without departing from the scope of the claimed subject matter. All such modifications and changes are intended to fall within the scope of the subject matter, as defined by the appended claims.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. As used in this specification and the appended claims, the singular forms "a," "an," and "the" include plural references unless the context clearly dictates otherwise. Any reference to "or" herein is intended to encompass "and/or" unless otherwise stated.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an"

limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method comprising:
   introducing a fluid comprising a plurality of cells into a flowcell of a cartridge positioned within a loading station, the flowcell comprising a fluidic channel, an inlet port, and an outlet port, wherein the fluidic channel comprises a bottom comprising a plurality of microwells, wherein the liquid is introduced into the inlet port of the flowcell and flowed across the plurality of microwells;
   introducing a fluid comprising plurality of magnetic barcode-bearing beads into the flowcell, wherein the fluid is introduced into the inlet port of the flowcell and flowed across the plurality of microwells, wherein each microwell is dimensioned to receive at least one cell of the plurality of cells and at least one magnetic barcode-bearing bead of the plurality of magnetic barcode-bearing beads;
   moving a first magnet of the loading station to a position sufficient to exert a first magnetic force on at least some of the magnetic barcode-bearing beads positioned within the plurality of microwells in a first direction;
   moving a second magnet of the loading station to a position sufficient to exert a second magnetic force on at least some of the magnetic barcode-bearing beads positioned within the plurality of microwells in a second direction different than the first direction; and
   introducing a fluid into the flowcell to cause at least some of the barcode-bearing beads to flow through the flowcell and out of the flowcell through the outlet port.

2. The method of claim 1, wherein at least one of the first magnetic force and the second magnetic force are of a magnitude sufficient to prevent magnetic barcode-bearing beads on which the at least one of the first magnetic force and second magnetic force are exerted from flowing through the flowcell when the fluid is introduced into the flowcell.

3. The method of claim 1, wherein each of the first magnet and the second magnet are coupled to an actuation mechanism comprising an actuator.

4. The method of claim 3, wherein moving the first magnet of the loading station to exert a first magnetic force on at least some of the magnetic barcode-bearing beads positioned within the plurality of microwells in a first direction comprises moving the actuator to a first actuator position.

5. The method of claim 4, wherein moving the second magnet of the loading station to exert a second magnetic force on at least some of the magnetic barcode-bearing beads positioned within the plurality of microwells in a second direction different than the first direction comprises moving the actuator to a second actuator position from the first actuator position.

6. The method of claim 5, wherein moving the actuator from the first actuator position to the second actuator position causes the first magnet to move to a position in which less magnetic force is exerted on the at least some of the magnetic barcode-bearing beads positioned within the plurality of microwells by the first magnet than when the actuator is positioned within the first position.

7. The method of claim 5, wherein moving the actuator from the first actuator position to the second actuator position causes the second magnet to move to position in which more magnetic force is exerted on the at least some of the magnetic barcode-bearing beads positioned within the plurality of microwells by the second magnet than when the actuator is positioned within the first position.

8. The method of claim 1, wherein moving the first magnet of the loading station to the position sufficient to exert the first magnetic force on at least some of the magnetic barcode-bearing beads positioned within the plurality of microwells in the first direction comprises moving the first magnet to a position inferior to the flowcell.

9. The method of claim 1, wherein moving the second magnet of the loading station to the position sufficient to exert the second magnetic force on at least some of the magnetic barcode-bearing beads positioned within the plurality of microwells in the second direction different than the first direction comprises moving the second magnet to a position superior to the flowcell.

10. The method of claim 1, wherein the method further comprises lysing cells in the plurality of the microwells between moving of the first and second magnets.

11. The method of claim 1, wherein the method further comprises positioning the cartridge in the loader.

12. A method comprising:
  introducing a fluid comprising a plurality of cells into a flowcell of a cartridge positioned within a loading station, the flowcell comprising a fluidic channel, an inlet port, and an outlet port, wherein the fluidic channel comprises a bottom comprising a plurality of microwells, wherein the liquid is introduced into the inlet port of the flowcell and flowed across the plurality of microwells so that cells are positioned in the microwells;
  introducing a fluid comprising a plurality of magnetic nucleic acid barcode-bearing beads into the flowcell, wherein the fluid is introduced into the inlet port of the flowcell and flowed across the plurality of microwells, wherein each microwell is dimensioned to receive at least one cell of the plurality of cells and at least one magnetic nucleic acid barcode-bearing bead of the plurality of magnetic barcode-bearing beads;
  moving a first magnet of the loading station from a first magnet inactive position to a position inferior to the flow cell sufficient to exert a first magnetic force on at least some of the magnetic nucleic acid barcode-bearing beads positioned within the plurality of microwells to maintain the at least some of the magnetic barcode-bearing beads positioned within the plurality of microwells;
  lysing cells positioned within the plurality of microwells;
  moving a second magnet of the loading station from a second magnet inactive position to a position superior to the flow cell to exert a second magnetic force on at least some of the magnetic nucleic acid barcode-bearing beads positioned within the plurality of microwell; and
  introducing a fluid into the flowcell through the inlet port to cause at least some of the magnetic nucleic acid barcode-bearing beads to flow through the flowcell and out the outlet port.

13. The method of claim 12, wherein the method further comprises moving the first magnet to the first magnet inactive position following lysing.

14. The method of claim 12, wherein the method further comprises moving the second magnet to the second magnet inactive before introducing the fluid into the flowcell through the inlet port to cause at least some of the magnetic nucleic acid barcode-bearing beads to flow through the flowcell and out the outlet port.

15. The method of claim 12, wherein the lysing comprises introducing lysing buffer into the inlet port of the flowcell and flowing the lysis buffer across the plurality of microwells.

16. The method of claim 12, wherein the method further comprises, following lysing cells, introducing a wash fluid into the inlet port of the flow cell and flowing the wash fluid across the plurality of microwells.

17. The method of claim 12, wherein the method further comprises, introducing a wash fluid into the inlet port of the flow cell and flowing the wash fluid across the plurality of microwells with the second magnet is in the position superior to the flowcell.

18. The method of claim 12, wherein each of the first magnet and the second magnet are coupled to an actuation mechanism comprising an actuator.

19. The method of claim 12, wherein moving the first magnet of the loading station to inferior position comprises moving the actuator to a first actuator position moving the second magnet of the loading station to superior position comprises moving the actuator to a second actuator position from the first actuator position.

20. The method of claim 12, wherein the method further comprises positioning the cartridge in the loader.

* * * * *